US007205008B2

(12) United States Patent
Castillo et al.

(10) Patent No.: US 7,205,008 B2
(45) Date of Patent: Apr. 17, 2007

(54) **METHODS OF TREATING ALZHEIMER'S DISEASE AND OTHER AMYLOIDOSES USING *HYPERICUM PERFORATUM* AND DERIVATIVES THEREOF**

(75) Inventors: Gerardo Castillo, Seattle, WA (US); Alan D. Snow, Lynnwood, WA (US)

(73) Assignee: ProteoTech, Inc., Kirkland, WA (US)

(\*) Notice: Subject to any disclaimer, the term of this patent is extended or adjusted under 35 U.S.C. 154(b) by 0 days.

(21) Appl. No.: 10/108,235

(22) Filed: Mar. 26, 2002

(65) Prior Publication Data

US 2002/0150637 A1    Oct. 17, 2002

Related U.S. Application Data

(62) Division of application No. 09/525,787, filed on Mar. 15, 2000, now abandoned.

(51) Int. Cl.
*A01N 65/00* (2006.01)
(52) U.S. Cl. ...................................... 424/730
(58) Field of Classification Search ................ 424/730, 424/724
See application file for complete search history.

(56) References Cited

U.S. PATENT DOCUMENTS 6,322,824 B1 \* 11/2001 Chatterjee et al. .......... 424/730

FOREIGN PATENT DOCUMENTS

WO    WO 99/40905    \*    8/1999

OTHER PUBLICATIONS

Puchitler et al. "On the Binding of Congo Red by Amyloid," pp. 355-364, Sep. 1961. (vol. No. not available.).
Benson et al. "Serum Amyloid a Protein in Amyloidosis, Rheumatic, and Neoplastic Diseases," Arthritis and Rheumatism, vol. 22, No. 1, pp. 36-42, Jan. 1979.
Kamei et al. "Amyloidosis Associated with Juvenile Rheumatoid Arthritis," Acta Pathol. Japan. vol. 32 (1), pp. 123-133, 1982.
McDam et al. "Association of Amyloidosis with Erythema Nodosum Leprosum Reactions and Recurrent Neutrophil Leucocytosis in Leprosy," The Lancet, pp. 572-575, Sep. 1975. (vol. No. not available.).
Metaxas et al. "Familial Mediterranean Fever and Amyloidosis," Kidney International, vol. 20, pp. 676-685, 1981.
Harada et al. "Human Amyloid Protain: Chemical Variability and Homogeneity," The Journal of Histochemistry and Cytochemistry, vol. 19, No. 1 pp. 1-15, Jun. 1971.
Johnson et al. "Islet Amyloid, Islet-Amyloid polypeptide, and Diabetes Mellitus," The New England Journal of Medicine. vol. 321, No. 8 pp. 513-518, Aug. 1989.
Johnson et al. "Islet Amyloid Polypeptide: Mechanisms of Amyloidogenesis in the Pancreatic Islets and Potential Roles in Diabetes Mellitus," Laboratory Investigation, vol. 66, No. 5, pp. 522-534, 1992.
Gejyo et al. "A New Form of Amyloid Protein Associated with Chronic Hemodialysis was Identified as $\beta_2$-Microglobulin," Biochemical and Biophysical Research Communications, vol. 129 No. 3, pp. 701-706, Jun. 1985.
Gejyo et al. "$\beta_2$—Microglobulin: A New Form of Amyloid Protein Associated with Chronic Hemodialysis," Kidney International, vol. 30, pp. 385-389, 1986.
Skinner et al. "The Prealbumin Nature of the Amyloid Protein in Familial Amyloid Polyneuropathy (FAP)-Swedish Variety," Biochemical and Biophysical Research Communications, vol. 99. No. 4, pp. 1326-1332, Apr. 1981.
Joao et al. "Studies on Plasma Transthyretin (prealbumin) in Familial Amyloidotic Polyneuropathy Portuguese Type," Journal of Laboratory Clinic Medicine, vol. 102, No. 4, pp. 590-603, Oct. 1983.
Joso et al. "Amyloid Fibril Protein in Familial Amyloidotic Polyneuropathy, Portugese Type," Journal of Clinical Investigation, vol. 74, pp. 104-109, Jul. 1984.
Tawara et al. "Amyloid Fibril Protein in Type I Familial Amyloidotic Polyneuropathy in Japanese," Journal of Laboratory Clinical Medicine, vol. 98. No. 6, pp. 811-822, Dec. 1981.
Cutler et al. "Tacrine in Alzheimer's Disease," The New England Journal of Medicine, vol. 328. No. 11, pp. 808-810, Mar. 1992.
Barner et al. "Donepezil Use in Alzheimer Disease," The Annals of Pharmacotherapy, vol. 32. pp. 70-77, Jan. 1998.
Flood et al. "Amnestic Effects in Mice of Four Synthetic Peptides Homologous to Amyloid $\beta$ Protein from Patients with Alzheimer Disease," Procedure of National Academy of Science. vol. 88. pp. 3363-3366. Apr. 1991.
Flood et al. "An Amyloid $\beta$-protein Fragment, A$\beta$[12-28], Equipotently Impairs Post-Training Memory Processing when Injected into Different Limbic System Structures," Brain Research vol. 663. pp. 271-276. 1994.
Broeckhoven et al. "Amyloid $\beta$ Protein Precursor Gene and Hereditary Cerebral Hemorrhage with Amyloidosis (Dutch)," Science, vol. 248. pp. 1120-1122, no date of publication is available.

(Continued)

*Primary Examiner*—Herbert J. Lilling
(74) *Attorney, Agent, or Firm*—Patrick M Dwyer

(57) ABSTRACT

A method for inhibiting the formation or persistence of brain amyloid deposits in a patient, including administering to the patient a therapeutically effective amount of plant matter from a plant of the genus *Hypericum*, species *perforatum*.

6 Claims, 6 Drawing Sheets

OTHER PUBLICATIONS

Murrell et al. "A Mutation in the Amyloid Precursor Protein Associated with Hereditary Alzheimer's Disease," Reports, Oct. 1991.

Haass et al. "The Swedish Mutation Causes Early-onset Alzheimer's Disease by β-secretase Cleavage Within the Secretory Pathway," Nature Medicine, vol. 1, pp. 1291-1296. No. 12 Dec. 1995.

Hardy et al. "Framing β-amyloid," Nature Genetics, vol. 1, pp. 233-234. Jul. 1992.

Wagner et al. "Inhibition of MAO by Fractions and Constituents of Hypericum Extract," Journal of Geriatric Psychiatry and Neurology, vol. 7 Suppl. 1. pp. S57-S59. Oct. 1994.

Thiede et al. "Inhibition of MAO and COMT by Hypericum Extracts and Hypericin," Journal of Geriatric Psychiatry and Neurology, vol. 7, Suppl. 1 pp. S54-S56. Oct. 1994.

Kerb et al. "Single-Dose and Steady-State Pharmacokinetics of Hypericin and Pseudohypercin," Antimicrobal Agents and Chemotherapy vol. 40. No. 9 pp. 2087-2093. Sep. 1996.

Lavie et al. "Hypericin as an Inactivator of Infectious Viruses in Blood Components," Transfusion vol. 35 No. 5 pp. 392-400 1995.

Schulz et al. "Effects of Hypericum Extract on the Sleep EEG in Older Volunteers," Journal of Geriatric Psychiatry and Neurology vol. 7 Suppl.1 pp. S39-S43. Oct. 1994.

Holden et al. "Treating AIDS With Warts," Science, vol. 254, pp. 522, no date of publication is available.

Vanderwerf et al. "Hypericin: A New Laser Phototargeting Agent for Human Cancer Cells," Laryngoscope vol. 106 pp. 479-483. Apr. 1996.

Naiki et al. "Kinetic Analysis of Amyloid Fibril Polymerization In Vitro" Laboratory Investigator vol. 65, No. 1, pp. 104-110, 1991.

Levine et al. "Thioflavine T Interaction with synthetic Alzheimer's disease β-amyloid peptides: Detection of amyloid aggregation in solution", Protein Science, vol. 2, pp. 404-410, 1993.

Levine et al. "Thioflavine T Interaction with Amyloid β-sheet Structures", International Journal Experimental Clinical Investigation, vol. 2, pp. 1-6. 1995.

Naiki et al. "First-Order Kinetic Model of Alzheimer's β-Amyloid Fibril Extension In Vitro," Laboratory Investigation, vol. 74, No. 2, pp. 374-383, Feb. 1996.

Snow et al. "Proteoglycans in the Pathogenesis of Alzheimer's Disease and Other Amyloidoses," Neurobiology of Aging, vol. 10, pp. 481-497. Apr. 1989.

Castillo et al. "Perlecan Binds to the β-Amyloid Proteins (Aβ) of Alzheimer's Disease, Accelerates Aβ Fibril Formation, and Maintains Aβ Fibril Stability," Journal of Neurochemistry vol. 69 pp. 2452-2465. 1997.

Glenner et al. "Alzheimer's Disease: Initial Report of the Purification and Characterization of a Novel Cerebrovascular Amyloid Protein," Biochemical and Biophysical Research Communications, vol. 120. No. 3 pp. 885-890, May 1984.

Colin et al. "Amyloid Plaque Core Protein in Alzheimer Disease and Down Syndrome," Medical Sciences, vol. 82, pp. 4245-4249, Jun. 1985.

WHO-IUIS Nomenclture Sub-Committee "Nomenclature of Amyloid and Amyloidosis," Bulletin of the World Health Organization, vol. 71 (1), pp. 105-108, 1993.

Tanzi et al. "Protease Inhibitor Domain Encoded by an Amyloid Protein Precursor mRNA Associated with Alzheimer's Disease," Nature, vol. 331. pp. 528-532, 1988.

Kitaguchi et al. "Novel Precursor of Alzheimer's Disease Amyloid Protein Shows Protease Inhibitory Activity," Nature, vol. 331, pp. 530-532, Feb. 1988.

Ponte et al. "A New A4 Amyloid mRNA Contains a Domain Homologous to Serine Proteinase Inhibitors," Nature, vol. 331. pp. 525-527, no date of publication is available.

Grundke-Iqbal et al. "Abnormal Phosphorylation of the Microtubule-Associated Protein t (Tau) in Alzheimer Cytoskeletal Pathology," Procedure of National Academy of Science, vol. 83. pp. 4913-4917, 1986.

Kosik et al. "Microtubule-associated Protein Tau (t) is a major antigenic component of paired helical filaments in Alzheimer disease," Procedure of Natural Academy of Science, vol. 83. pp. 4044-4048, Jun. 1986.

Lee et al. "A68: A Major Subunit of Paired Helical Filaments and Derivatized Forms of Normal Tau," Science, vol. 251. pp. 675-678, Feb. 1991.

Mandybur "Cerebral Amyloid Angiopathy: The Vascular Pathology and Complications," Journal of Newropathology and Experimental Neurology, vol. 45. No. 1 pp. 79-90, Jan. 1986.

Pardridge et al. Amyloid Angiopathy of Alzheimer's Disease: Amino Acid Composition and Partial Sequence of a 4,200-Dalton Peptide Isolated from Cortical Microvessels, Journal of Neurochemistry, vol. 49 No. 5. pp. 1394-1401, 1987.

Pike et al. "In Vitro Aging of β-Amyloid Protein Causes Peptide Aggregation and Neurotoxicity," Brain Research. vol. 563. pp. 311-314, 1991.

Pike et al. "Structure-Activity Analyses of β-Amyloid Peptides: Contributions of the β25-35 Region to Aggregation and Neurotoxicity," Journal of Neurochemistry. vol. 64. No. 1 pp. 253-265. 1995.

Harrigan et al. "Beta Amyloid is Neurotoxic in Hippocampal Slice Cultures," Neurobiology of Aging. vol. 16. No. 5. pp. 779-789. 1995.

Games et al. "Alzheimer-type Neuropathology in Transgenic Mice Overexpressing V717F β-amyloid Precursor Protein," Nature vol. 373. pp. 523-527. Feb. 1995.

Hsiao et al. "Correlative Memory Deficits, Aβ Elevation, and Amyloid Plaques in Transgenic Mice," Science. vol. 274. pp. 99-102. Oct. 1996.

Tamaoka et al. "Amyloid β-protein 1-42/43 (Aβ 1-42/43) in Cerebellar Diffuse Plaques: Enzyme-linked Immunosorbent Assay and Immunocytochemical," Brain Research vol. 679 pp. 151-156. 1995.

Tamaoka et al. "Biochemical Evidence for the Long-Tail Form (Aβ1-42/43) of Amyloid β-protein as a Seed Molecule in Cerebral Deposit of Alzheimer's Disease," Biochemical and Biophysical Research Communication, vol. 205 No. 1 pp. 834-842 Nov. 1994.

Cooper et al. "Purification and Characterization of a Peptide from Amyloid-rich Pancreases of Type 2 Diabetic Patients," Procedure of National Academy of Science vol. 84 pp. 8628-8632 Dec. 1987.

Database Biosis on Medline, (Columbus, OH, USA), AN 1999:33587, Melikian et al, "Hypericin Content in St. John's Wort (Hypericum Perforatum L.) Growing in Armenia", abstract, Pharmaceutical and Pharmacological Letters, Sep. 1998, vol. 8, No. 3, pp. 101-102.

Database Napralert on STN (Columbus, OH, USA), Demisch et al, "Identification of Selective MAO-Type-A Inhibitors in Hypericum Perforatum L. (Hyperforat)", abstract, Pharmacopsychiatry, 1989.

* cited by examiner

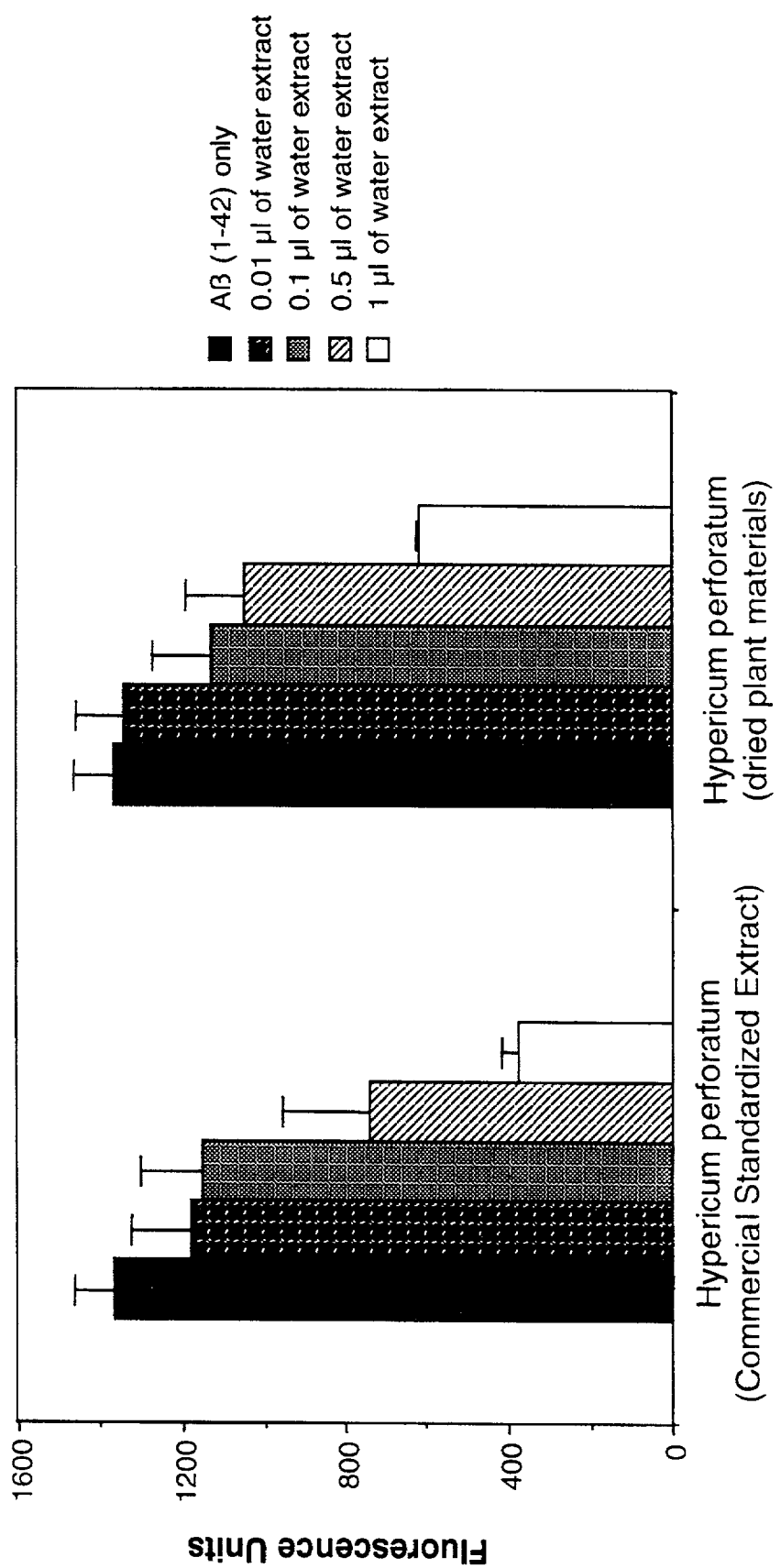

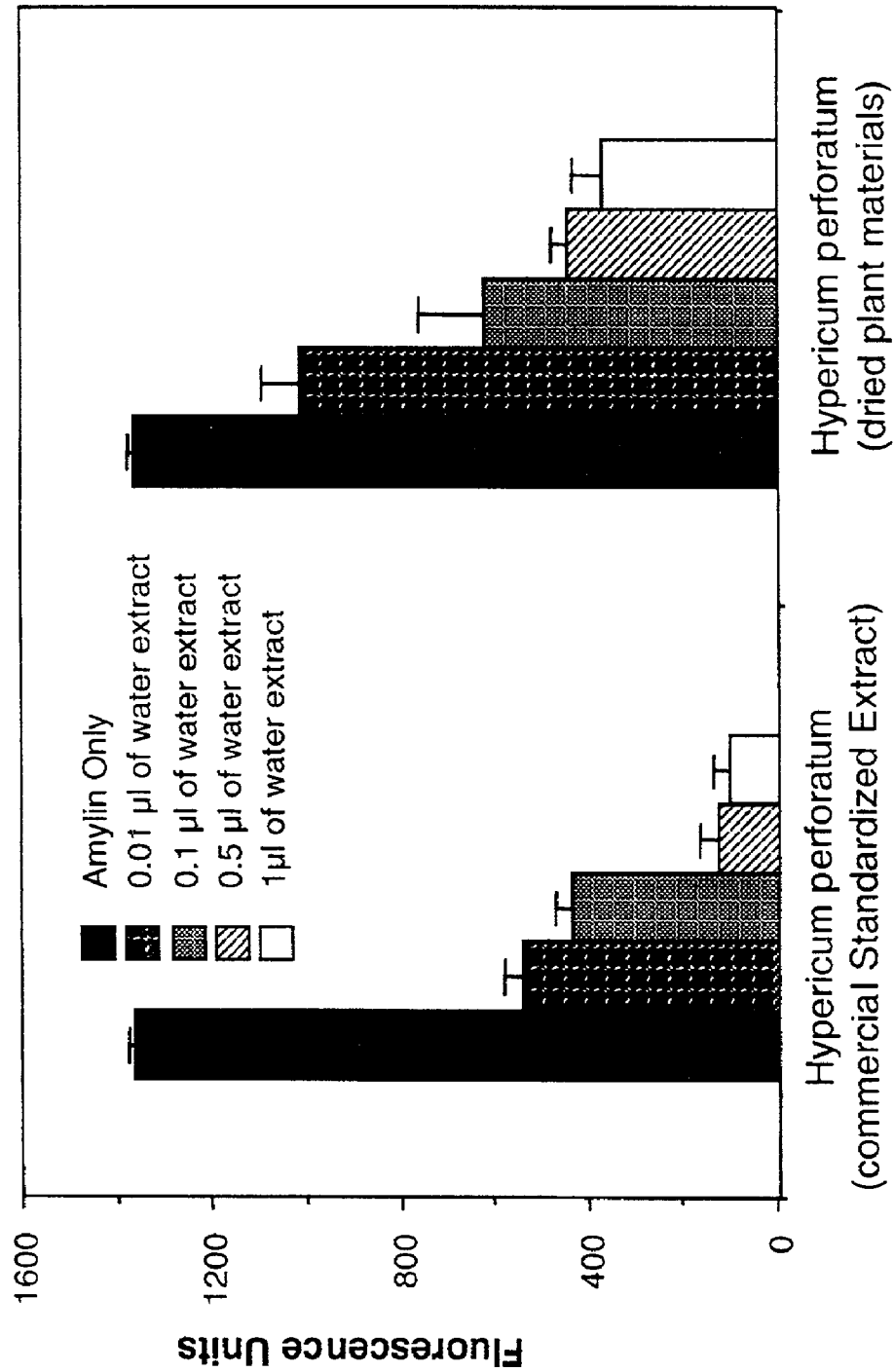

METHODS OF TREATING ALZHEIMER'S DISEASE AND OTHER AMYLOIDOSES USING *HYPERICUM PERFORATUM* AND DERIVATIVES THEREOF

This is a Divisional application of Ser. No. 09/525,787 filed Mar. 15, 2000 now abandoned.

TECHNICAL FIELD

The invention relates to compositions and methods for treating Alzheimer's Disease and other amyloidoses, and to methods for isolating pharmaceutical agents from plant matter; more particularly, it relates to compositions and methods for therapeutic intervention in Alzheimer's disease and other amyloidoses using plant matter and derivatives thereof.

BACKGROUND OF THE INVENTION

Alzheimer's disease is characterized by the accumulation of a 39–43 amino acid peptide termed the beta-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid as a major causative factor of Alzheimer's disease pathogenesis.

A variety of other human diseases also demonstrate amyloid deposition and usually involve systemic organs (i.e. organs or tissues lying outside the central nervous system), with the amyloid accumulation leading to organ dysfunction or failure. In Alzheimer's disease and "systemic" amyloid diseases, there is currently no cure or effective treatment, and the patient usually dies within 3 to 10 years from disease onset.

New compounds or agents for therapeutic regimes to arrest or reverse amyloid formation, deposition, accumulation and/or persistence that occurs in Alzheimer's disease and other amyloidoses are therefore desperately sought.

DISCLOSURE OF THE INVENTION

A primary object of the present invention is to establish new methods for the treatment of the amyloid diseases. The amyloid diseases include, but are not limited to, the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Another object of the present invention is to use the plant *Hypericum perforatum* (also referred to as St. John's Wort) and/or its constituents thereof (including but not limited to its leaves, buds and flowers) for the treatment of amyloid formation, deposition, accumulation and/or persistence in Alzheimer's disease, type II diabetes and other amyloidoses. *Hypericum perforatum* is also referred to as, but not limited to, St. John's Wort, Hyperici herba, Amber, Goatweed, Johnswort, Klamath Weed, and Tipton Weed.

Another object of the present invention is to use extracts and/or derivatives thereof from plant matter related to the family Hypericaceae, which includes, but is not limited to the genus *Hypericum*, for the treatment of amyloid formation, deposition, accumulation and/or persistence in Alzheimer's disease, type II diabetes and other amyloidoses.

Another object of the present invention is to use extracts and/or derivatives thereof from plant matter related to the various *Hypericum* species, which may include but not limited to, *Hypericum perforatum, Hypericum calycinum, Hypericum formosum, Hypericum hirsutum, Hypericum patulum,* and *Hypericum olympicum.*

Another object of the present invention is to use commercially available pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, dried leaves, dried buds, dried flowers which contain *Hypericum perforatum* to treat patients with Alzheimer's disease, type II diabetes and other amyloidoses.

Another object of the present invention is to use *Hypericum perforatum*, and/or the hypericins contained within *Hypericum perforatum* for the treatment of amyloid formation, deposition, accumulation and/or persistence in Alzheimer's disease, type II diabetes and other amyloidoses.

Yet another object of the present invention is to use the flavanoids contained within *Hypericum perforatum* for the treatment of amyloid formation, deposition, accumulation and/or persistence in Alzheimer's disease, type II diabetes and other amyloidoses. Such flavanoids include, but are not limited to, hyperoside, biapigenin, rutin, quercetin, quercitin, isoquercitrin, pseudohypericin, hyperforin, procyanidines, amentoflavine, and luteolin.

Yet another object of the present invention is to use the xanthones contained within *Hypericum perforatum* for the treatment of amyloid formation, deposition, accumulation and/or persistence in Alzheimer's disease, type II diabetes and other amyloidoses.

Yet another object of the present invention is to use the proanthocyanidins contained within *Hypericum perforatum* for the treatment of amyloid formation, deposition, accumulation and/or persistence in Alzheimer's disease, type II diabetes and other amyloidoses.

Yet another object of the present invention is to use the dianthrones contained within *Hypericum perforatum* for the treatment of amyloid fonnation, deposition, accumulation and/or persistence in Alzheimer's disease, type II diabetes and other amyloidoses.

Yet another object of the present invention is to use the tannins contained within *Hypericum perforatum* for the treatment of amyloid formation, deposition, accumulation and/or persistence in Alzheimer's disease, type II diabetes and other amyloidoses.

Yet another object of the present invention is to use the carbohydrates contained within *Hypericum perforatum* for the treatment of amyloid formation, deposition, accumulation and/or persistence in Alzheimer's disease, type II diabetes and other amyloidoses. Such carbohydrates include, but are not limited to, pectin.

Yet another object of the present invention is to use the lipids contained within *Hypericum perforatum* for the treatment of amyloid formation, deposition, accumulation and/or persistence in Alzheimer's disease, type II diabetes and other amyloidoses. Such lipids include, but are not limited to, monoterpenes.

Yet another object of the present invention is to use the vitamins contained within *Hypericum perforatum* for the treatment of amyloid formation, deposition, accumulation and/or persistence in Alzheimer's disease, type II diabetes and other amyloidoses. Such vitamins include, but are not limited to, vitamin A and vitamin C.

Yet another object of the present invention is to provide methods to isolate the active ingredients present within *Hypericum perforatum* for use as potent agents which inhibit amyloid formation, amyloid deposition, amyloid accumulation, amyloid persistence, amyloid protein-amyloid protein interactions, and/or cause a dissolution/disruption of preformed or pre-deposited amyloid fibrils in Alzheimer's disease, type II diabetes and other amyloidoses. Methods for isolation of the active ingredients within *Hypericum perforatum* include application of some standard techniques known to those skilled in the art, including, but not limited to, thin layer chromatography using silica-coated plates, and separation and isolation using high pressure liquid chromatography (HPLC). Unknown active ingredients within *Hypericum perforatum* found to be potent inhibitors of amyloid formation, amyloid deposition, amyloid accumulation, amyloid persistence, amyloid protein-amyloid protein interactions, and/or cause a dissolution/disruption of preformed or pre-deposited amyloid fibrils in Alzheimer's disease, type II diabetes and other amyloidoses, are identified by retesting of individual bands or fractions (separated by thin layer chromatography, column chromatography and/or HPLC) using specific assay tests as described in the examples of the present invention. Sufficient isolation of these active ingredients contained within individual bands and/or fractions are then sent out for specific analyses which may include, but are not limited to, scanning electron microscope equipped with energy dispersive x-ray analyzer to detect and spatially map some elements present in each sample, elemental analysis by combustion to determine the relative % of carbon, hydrogen and nitrogen, high resolution mass spectroscopy to determine molecular weight and elemental composition, fourier transform infrared spectroscopy to determine functional groups and make comparisons to the spectra of known compounds, differential scanning calorimetry to determine melting point, atomic absorption, gel chromatography, high performance liquid chromatography, proton and $C^{13}$ nuclear magnetic resonance spectroscopy for material characterization and to provide information regarding the position of atoms relative to each other, and UV/VIS spectroscopy. It is expected that additional techniques will be developed as part of the further isolation of potent active ingredients within *Hypericum perforatum*.

Yet another object of the present invention is to provide the use of *Hypericum perforatum* and/or its ingredients [(regardless of commercial source and regardless of final form for consumption by humans, i.e. pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, dried leaves, dried buds, and dried flowers] for inhibition of amyloid formation, deposition, accumulation, and/or persistence, regardless of its clinical setting.

Yet another object of the present invention is to provide compositions and methods involving administering to a subject a therapeutic dose of *Hypericum perforatum* (or its active ingredients) which inhibits amyloid deposition. Accordingly, the compositions and methods of the invention are useful for inhibiting amyloidosis in disorders in which amyloid deposition occurs. The compounds of the invention can be used therapeutically to treat amyloidosis or can be used prophylactically in a subject susceptible to amyloidosis. The methods of the invention are based, at least in part, in directly inhibiting amyloid fibril formation, inhibiting amyloid fibril growth, and/or causing dissolution/disruption of preformed amyloid fibrils.

Yet another object of the present invention is to provide pharmaceutical compositions for treating amyloidosis. The pharmaceutical compositions include a therapeutic compound of the invention in an amount effective to inhibit amyloid deposition and a pharmaceutically acceptable vehicle.

Yet another object of the present invention is the use of any and all synthetic compounds made similar to *Hypericum perforatum* and/or its active ingredients for use as potent agents which inhibit amyloid formation, amyloid deposition, amyloid accumulation, amyloid persistence, amyloid protein-amyloid protein interactions, and/or cause a dissolution/disruption of pre-formed or pre-deposited amyloid fibrils in Alzheimer's disease, type II diabetes and other amyloidoses.

It is yet another object of the invention to meet any and all of the needs summarized above.

These and such other objects of the invention will become evident from the disclosure below are met by the invention disclosed herein.

Application of the invention to these needs is especially beneficial in that the invention is the only system that effectively provides for use of extracts from the leaves, flowers and/or buds of *Hypericum perforatum*, and use of the ingredients contained within the various commercial preparations of *Hypericum perforatum*, to benefit human patients with Alzheimer's disease and other amyloidoses due to *Hypericum perforatum*'s newly discovered ability to inhibit amyloid fibril formation, inhibit amyloid fibril growth, inhibit amyloid-proteoglycan interactions, amyloid-glycosaminoglycan interactions, and cause dissolution and/or disruption of preformed amyloid fibrils.

The present invention pertains to the identification and surprising discovery that an extract from the dried upper plant parts (i.e. leaves, flowers and/or buds) of *Hypericum perforatum*, otherwise known as St. John's Wort, act as an impressive inhibitor of Alzheimer's disease amyloid formation and growth. In addition, *Hypericum perforatum* also has the ability to inhibit amyloid protein-amyloid protein interactions, which are believed to be important for the growth of amyloid deposits in tissues. Furthermore, *Hypericum perforatum* also has the ability to inhibit amyloid protein-proteoglycan (PG)/glycosaminoglycan (GAG) interactions, which are believed to be important for the formation and persistence of all amyloid deposits in tissues. In addition, *Hypericum perforatum* has the ability to dissolve/disrupt pre-formed amyloid fibrils of the Alzheimer's and type II diabetes types, suggesting that this agent may be useful for patients at latter stages of both Alzheimer's disease, type II diabetes and other amyloidoses. *Hypericum perforatum* extracted from different commercial sources (extracts isolated from dried whole plant materials or from powder obtained from gelatin capsules containing a concentrated extract of 0.3% hypericin) were all found to serve as potent inhibitors of Alzheimer's disease amyloid fibrillogenesis.

While results are exemplified with *Hypericum perforatum*, other species of *Hypericum* are believed to have similar effect.

Commercially available *Hypericum perforatum* (extracts obtained from dried whole plant materials, or from gelatin-capsules containing 0.3% hypericin) caused a marked significant inhibition of Aβ amyloid fibril formation as determined using a Thioflavin T fluorometry assay. Extracts of *Hypericum perforatum* obtained from different commercial sources inhibited Aβ amyloid fibrillogenesis in a dose-dependent manner. *Hypericum perforatum* extract also inhibited Alzheimer's Aβ-Aβ interactions as determined using a solid phase binding assay demonstrating that *Hypericum perforatum* is additionally an effective inhibitor of Alzheimer's amyloid fibril growth. Furthermore, *Hypericum perforatum* was effective in the inhibition of Aβ-proteoglycan/glycosaminoglycan (PG/GAG) interactions (an important therapeutic target for all amyloidoses) as determined using a solid phase binding immunoassay. *Hypericum perforatum* extracts derived from different commercial sources was also a potent dissolving/inhibiting agent of pre-formed Aβ(1-40) or Aβ(1-42) containing amyloid fibrils, and pre-formed amylin fibrils, as determined using a Thioflavin T fluorometry and Congo red staining assays. This latter effect occurred in a dose-dependent manner, causing a significant dissolution of both Aβ1-40 and 1-42 pre-formed Alzheimer's fibrils within a 2 hour incubation duration. *Hypericum perforatum* which was effective in all of the studies described above were all derived from *Hypericum perforatum* extract obtained from whole plant (i.e. containing dried flowers, leaves and buds), and gelatin-capsule form, and were both currently available commercially for oral use in humans. Therefore, the present invention claims the use of *Hypericum perforatum* (in a pill, tablet or liquid form, and from dried plant materials) and derivatives thereof from different commercial sources for the treatment of amyloidosis in Alzheimer's disease, type II diabetes and other amyloidoses. Also disclosed are methods of isolation to identify and purify the key amyloid inhibitory ingredients within the plant material. Identification of the "active" amyloid inhibitory ingredients within the extracted plant materials are anticipated to lead to new drug design for anti-amyloid therapeutics of the future. Current use of *Hypericum perforatum* and its ingredients contained within different commercial preparations are anticipated to benefit human patients at all stages of Alzheimer's disease due to *Hypericum perforatum's* inherent ability to inhibit Aβ amyloid fibril formation (early to mid-stage Alzheimer's disease), inhibit amyloid fibril growth (early to mid-stage Alzheimer's disease), inhibit amyloid-PG/GAG interactions (all stages of Alzheimer's disease) and cause dissolution/disruption of preformed amyloid fibrils (mid to late stages of Alzheimer's disease). Similarly, *Hypericum perforatum* is anticipated to benefit patients with different systemic amyloid diseases such as type II diabetes, regardless of the stage of amyloid accumulation and the organ (or tissue) involved.

These and other features and advantages of the present invention will become more fully apparent when the following detailed description of the invention is read in conjunction with the accompanying figures.

In other aspects of the invention, a pharmaceutical agent is disclosed for treating an amyloid disease in a patient, wherein the pharmacological agent comprises a therapeutically effect amount of plant matter from the genus *Hypericum*. The pharmaceutical agent is preferably from a plant of the genus *Hypericum*, species *perforatum*. The pharmacological agent is preferably an extract obtained from *Hypericum perforatum*, the extract being derived from the dried leaves, flowers and buds of *Hypericum perforatum*, and advantageously taken from some commercially available source such as pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, or plant powder obtained from dried leaves, buds, and/or flowers.

In a preferred embodiment, the pharmaceutical agent is an amyloid inhibitory ingredient selected from the group consisting of, but not limited to, flavanoids, xanthones, proanthocyanidins, dianthrones, tannins, monoterpenes, hyperoside, biapigenin, rutin, quercetin, quercitin, isoquercitrin, pseudohypericin, hyperforin, procyanidines, amentoflavine, luteolin, pectin, vitamin A, and vitamin C.

The pharmacological agent preferably has a therapeutically effective amount of *Hypericum perforatum* in a dosage in the range of from about 10 to 1,000 mg/kg of body weight of the patient, and more preferably in the range of about 10 to 100 mg/kg of body weight of the patient.

The pharmacological agent preferably has a therapeutically effective amount of hypericin, standardized to contain hypericin at a range of 0.05% to 2%, but more preferably in the range of about 0.1% to 0.5%, per 250 mg to 500 mg capsule containing *Hypericum perforatum*.

The amyloid disease for treatment with the pharmacological agent is selected from the group consisting of the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $beta_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Preferred pharmaceutical agents have a weight percentage of plant extract in the agent is in the range of from about 70% to about 95%, and may also have a pharmaceutically acceptable carrier, diluent or excipient. The pharmaceutical agent preferably has an amyloid inhibitory activity or efficacy greater than 50%.

In addition, *Hypericum perforatum* has the ability to inhibit the formation of brain amyloid deposits in patients who accumulate brain amyloid deposits that occur during normal aging and in a variety of brain disorders including Alzheimer's disease; it will therefore promote mental alertness in such patients.

*Hypericum perforatum* has the ability to reduce, eliminate, prevent or inhibit or disrupt/dissolve amyloid fibril or protein deposits, brain associated amyloid fibril deposits or brain associated amyloid protein deposits, as well as amyloid fibril formation and growth or age associated amyloid fibril formation and growth, brain associated amyloid fibril formation and growth, and interaction of amyloid protein with glycosaminoglycans or proteoglycans; it will therefore promote mental acuity, promote mental alertness, provide nutritional support for age or related cognitive or memory decline, promote cognitive well being, support brain function, improve cognitive ability, mental performance or memory, promote concentration and mental sharpness, improve mental vitality, promote greater mental clarity and alertness, improve short term memory, reduce or reverse age associated cognitive or memory decline, support normal brain function, enhance learning or memory; improve concentration, enhance mental performance, reduce mental decline, reduce likelihood of age related brain disorders, and maintain good brain health.

*Hypericum perforatum* further has the ability to reduce, eliminate, prevent, inhibit or disrupt/dissolve amyloid fibril or protein deposits, as well as amyloid fibril formation and growth, pancreas associated amyloid fibril formation and growth, and interaction of amyloid protein with glycosaminoglycans or with proteoglycans; it will therefore support healthy pancreatic function and promote pancreatic function by helping to promote normal insulin function.

Another aspect of the invention is a method for isolating amyloid inhibitory constituents within *Hypericum perforatum* plant matter, the method comprising the following steps: a) extracting the plant matter with an organic solvent or water, b) concentrating the extract, c) removing insoluble materials, d) precipitating amyloid inhibitory constituents with organic solvent or water, e) recovering and redissolving the amyloid inhibitory constituents obtained in organic solvent or water, and f) injecting and separation by HPLC.

The plant matter is preferably comprised of commercially obtained pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, or plant matter which contain *Hypericum perforatum*, extracts or derivatives thereof, and may be taken from commercially available gelatin-coated capsules which contain dried-plant material (preferably leaves, buds and flowers) of *Hypericum perforatum*, extracts or derivatives thereof.

A method is also disclosed for treating an amyloid disease in a patient, comprising the step of administering to the patient a therapeutically effective amount of plant matter from the plant of the genus *Hypericum*, species *perforatum*. The plant matter is preferably administered orally or by aerosol spray or in a parenterally injectable or infusible form.

The therapeutically effective amount of plant matter is preferably an amyloid inhibitory ingredient selected from the group consisting of but not limited to, flavanoids, xanthones, proanthocyanidins, dianthrones, tannins, monoterpenes, hyperoside, biapigenin, rutin, quercetin, quercitin, isoquercitrin, pseudohypericin, hyperforin, procyanidines, amentoflavine, luteolin, pectin, vitamin A, and vitamin C.

BRIEF DESCRIPTION OF THE DRAWINGS

The following drawings are illustrative of the invention and are not meant to limit the scope of the invention.

FIG. 5 is a black and white graph of a Thioflavin T fluorometry assay utilized to determine the potential dose-dependent effects of *Hypericum perforatum* on dissolution/disruption of pre-formed Alzheimer's Aβ1-42 amyloid fibrils within a 2 hour incubation period. *Hypericum perforatum* (derived either from an extract obtained from dried plant materials, or from an extract obtained from the powder present in commercially available gelatin-capsules which contain 0.3% hypericin) causes dissolution of pre-formed Alzheimer's Aβ1-42 amyloid fibrils in a dose-dependent manner.

FIG. 6 is a black and white graph of a Thioflavin T fluorometry assay utilized to show that an *Hypericum perforatum* (derived either from an extract obtained from dried plant materials, or from an extract obtained from the powder present in commercially available gelatin-capsules which contain 0.3% hypericin) is also able to cause a significant dissolution of pre-formed islet amyloid fibrils (ie. amylin).

BEST MODE OF CARRYING OUT THE INVENTION

Figure 1:
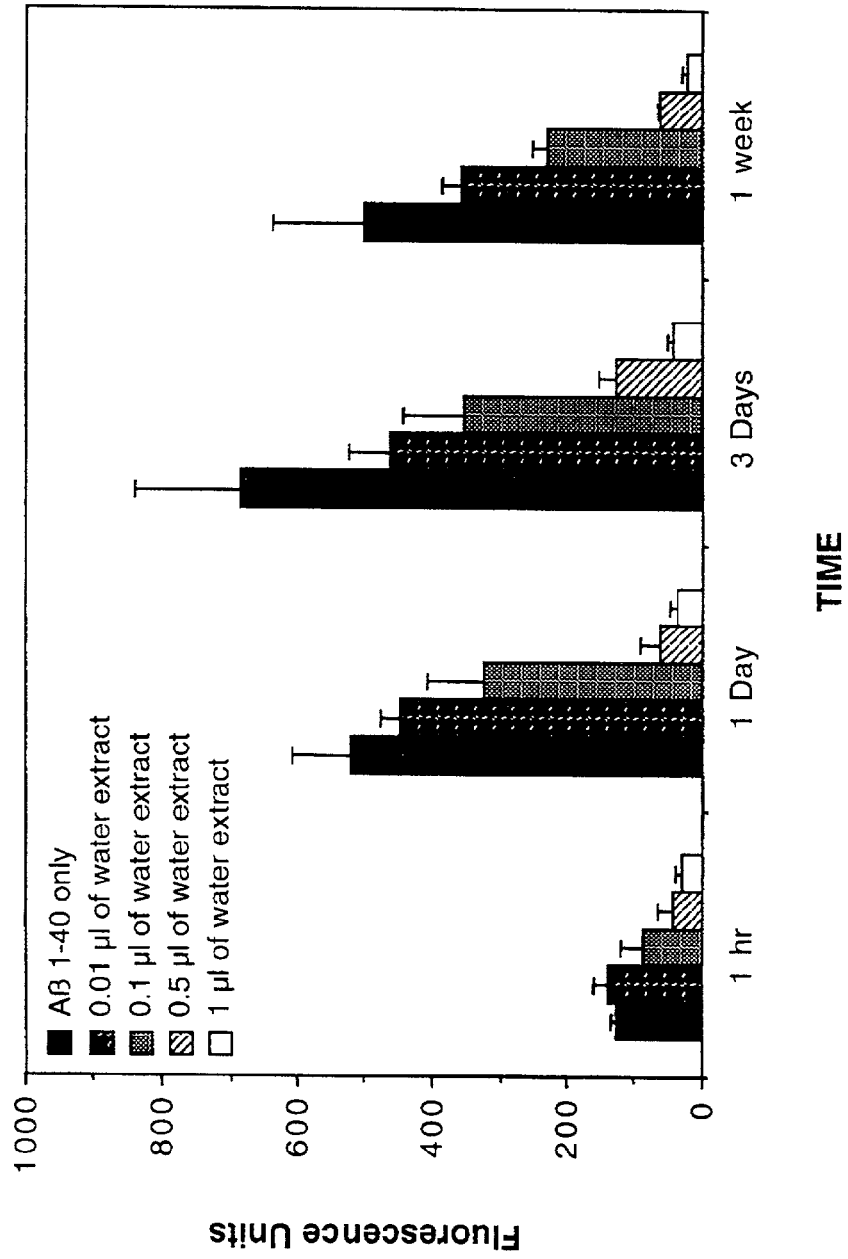
FIG. 1 is a black and white graph of a 1 week Thioflavin T fluorometry assay demonstrating that an extract from *Hypericum perforatum* (derived from a commercial source) causes dose-dependent inhibition of Alzheimer's disease Aβ1-40 amyloid fibril formation.

Turning now to the drawings, the invention will be described in a preferred embodiment by reference to the numerals of the drawing figures wherein like numbers indicate like parts.

Amyloid and Amyloidosis

Amyloid is a generic term referring to a group of diverse, but specific extracellular protein deposits which all have common morphological properties, staining characteristics, and x-ray diffraction spectra. Regardless of the nature of the amyloid protein deposited all amyloids have the following characteristics: 1) an amorphous appearance at the light microscopic level and appear eosinophilic using hematoxylin and eosin stains; 2) all stain with Congo red and demonstrate a red/green birefringence as viewed under polarized light (Puchtler et al., *J. Histochem. Cytochem.* 10:355–364, 1962), 3) all contain a predominant beta-pleated sheet secondary structure, and 4) ultrastructurally amyloid usually consist of non-branching fibrils of indefinite length and with a diameter of 7–10 nm.

Amyloid today is classified according to the specific amyloid protein deposited. The amyloid diseases include, but are not limited to, the amyloid associated with Alzheimer's disease, Down's syndrome and Hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflamation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as prealbumin or transthyretin amyloid), and the amyloid associated with endocrine tumors such as medullary carcinoma of the thyroid (wherein the specific amyloid is referred to as variants of procalcitonin).

Although amyloid deposits in clinical conditions share common physical properties relating to the presence of a beta-pleated sheet conformation, it is now clear that many different chemical types exist and additional ones are likely to be described in the future. It is currently thought that there are several common pathogenetic mechanisms that may be operating in amyloidosis in general. In many cases, a circulating precursor protein may result from overproduction of either intact or aberrant molecules (ex. plasma cell dyscrasias), reduced degradation or excretion (serum amyloid A in some secondary amyloid syndromes and beta$_2$-microglobulin in long-term hemodialysis), or genetic abnormalities associated with variant proteins (ex. familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location. What are the precise mechanisms involved, and the aberrant causes leading to changes in proteolytic processing and/or translational modifications is not known in most amyloids.

Systemic amyloids which include the amyloid associated with chronic inflammation, various forms of malignancy and Familial Mediterranean Fever (ie. AA amyloid or inflammation-associated amyloidosis)(Benson and Cohen, *Arth. Rheum.* 22:36–42, 1979; Kamei et al, *Acta Path. Jpn.* 32:123–133, 1982; McAdam et al, *Lancet* 2:572–573, 1975; Metaxas, *Kidney Int.* 20:676–685, 1981), and the amyloid associated with multiple myeloma and other B-cell dyscrasias (ie. AL amyloid)(Harada et al, *J. Histochem. Cytochem.* 19:1–15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513–518, 1989). For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3–5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes (Johnson et al, *N. Engl. J. Med.* 321: 513–518, 1989; *Lab. Invest.* 66:522–535, 1992); the beta$_2$-microglobulin amyloid deposits in the medial nerve leading to carpal tunnel syndrome as observed in patients undergoing long-term hemodialysis (Geyjo et al, *Biochem. Biophys. Res. Comm.* 129:701–706, 1985; *Kidney Int.* 30:385–390, 1986); the prealbumin/transthyretin amyloid observed in the hearts of patients with senile cardiac amyloid; and the prealbumin/transthyretin amyloid observed in peripheral nerves of patients who have Familial Amyloidotic Polyneuropathy (Skinner and Cohen, *Biochem. Biophys. Res. Comm.* 99:1326–1332, 1981; Saraiva et al, *J. Lab. Clin. Med.* 102:590–603, 1983; *J. Clin. Invest.* 74:104–119, 1984; Tawara et al, *J. Lab. Clin. Med.* 98:811–822, 1989).

Alzheimer's Disease and the Aging Population

Alzheimer's disease is a leading cause of dementia in the elderly, affecting 5–10% of the population over the age of 65 years (*A Guide to Understanding Alzheimer's Disease and Related Disorders*, edited by Jorm, New York University Press, New York, 1987). In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease today affects 4–5 million Americans, with slightly more than half of these people receiving care at home, while the others are in many different health care institutions. The prevalence of Alzheimer's disease and other dementias doubles every 5 years beyond the age of 65, and recent studies indicate that nearly 50% of all people age 85 and older have symptoms of Alzheimer's disease (1997 *Progress Report on Alzheimer's Disease*, National Institute on Aging/National Institute of Health). 13% (33 million people) of the total population of the United States are age 65 and older, and this % will climb to 20% by the year 2025 (1997 *Progress Report on Alzheimer's Disease*, National Institute on Aging/National Institute of Health).

Alzheimer's disease also puts a heavy economic burden on society as well. A recent study estimated that the cost of caring for one Alzheimer's disease patient with severe cognitive impairments at home or in a nursing home, is more than $47,000 per year (*A Guide to Understanding Alzheimer's Disease and Related Disorders*, edited by Jorm, New York University Press, New York, 1987). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (1997 *Progress Report on Alzheimer's Disease*, National Institute on Aging/National Institute of Health).

Tacrine hydrochloride ("Cognex"), the first FDA approved drug for Alzheimer's disease is a acetylcholinesterase inhibitor (Cutler and Sramek, *N. Engl. J. Med.* 328: 808–810, 1993). However, this drug has showed limited success in the cognitive improvement in Alzheimer's disease patients and initially had major side effects such as liver toxicity. The second more recently FDA approved drug, donepezil (also known as "Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70–77, 1998; Rogers and Friedhoff, *Eur. Neuropsych.* 8:67–75, 1998), but is not believed to be a cure. Therefore, it is clear that there is a need for more effective treatments for Alzheimer's disease patients.

Amyloid as a Therapeutic Target for Alzheimer's Disease

Alzheimer's disease is characterized by the deposition and accumulation of a 39–43 amino acid peptide termed the beta-amyloid protein, Aβ or β/A4 (Glenner and Wong, *Biochem. Biophys. Res. Comm.* 120:885–890, 1984; Masters et al, *Proc. Natl. Acad. Sci. USA* 82:4245–4249, 1985; Husby et al, *Bull WHO* 71:105–108, 1993). Aβ is derived from larger precursor proteins termed beta-amyloid precursor proteins (or βPPs) of which there are several alternatively spliced variants. The most abundant forms of the βPPs include proteins consisting of 695, 751 and 770 amino acids (Tanzi et al, *Nature* 331:528–530, 1988; Kitaguchi et al, *Nature* 331:530–532, 1988; Ponte et al, *Nature* 331:525–527, 1988). The small Aβ peptide is a major component which makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). The pathological hallmarks of Alzheimer's disease is therefore the presence of "plaques" and "tangles", with amyloid being deposited in the central core of plaques. The other major type of lesion found in the Alzheimer's disease brain is the accumulation of amyloid in the walls of blood vessels, both within the brain parenchyma and in the walls of meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90, 1986; Pardridge et al, *J. Neurochem.* 49:1394–1401, 1987).

For many years there has been an ongoing scientific debate as to the importance of "amyloid" in Alzheimer's disease and whether the "plaques" and "tangles" characteristic of this disease, were a cause or merely the consequences of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al, *Br. Res.* 563: 311–314, 1991; *J. Neurochem.* 64:253–265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al, *Neurobiol. Aging* 16:779–789, 1995) and induces nerve cell death in transgenic mice (Games et al, *Nature* 373:523–527, 1995; Hsiao et al, *Science* 274:99–102, 1996). Injection of the Alzheimer's Aβ into rat brain also causes memory impairment and neuronal dysfunction (Flood et al, *Proc. Natl. Acad. Sci.* 88:3363–3366, 1991; *Br. Res.* 663:271–276, 1994). Probably, the most convincing evidence that Aβ amyloid is directly involved in the pathogenesis of Alzheimer's disease comes from genetic studies. It has been discovered that the production of Aβ can result from mutations in the gene encoding, its precursor, beta-amyloid precursor protein (Van Broeckhoven et al, *Science* 248:1120–1122, 1990; Murrell et al, *Science* 254:97–99, 1991; Haass et al, *Nature Med.* 1:1291–1296, 1995). The identification of mutations in the beta-amyloid precursor protein gene which causes early onset familial Alzheimer's disease is the strongest argument that amyloid is central to the pathogenetic process underlying this disease. Four reported disease-causing mutations have now been discovered which demonstrate the importance of Aβ in causing familial Alzheimer's disease (reviewed in Hardy, *Nature Genet.* 1:233–234, 1992). All of these studies suggest that providing a drug to reduce, eliminate or prevent fibrillar Aβ formation, deposition, accumulation and/or persistence in the brains of human patients is believed to serve as an effective therapeutic.

*Hypericum Perforatum* (St. John's Wort)

St. John's Wort, whose latin name is *Hypericum perforatum* belongs to the family Hypericaceae, which consists of eight genuses and about 350 species. The species of the *Hypericum* genus are widely distributed throughout the world, including more than 70 different species from India alone. *Hypericum perforatum* is native to the temperate zones of Europe and western Asia, but has become naturalized in North and South America as well as in Australia. This is a perennial plant, which by the second year of growth from seed reaches a height of about 30 inches. The many bright yellow flowers each contain about 50 stamens, which tend to group into three loosely-defined clumps.The lance-shaped, opposite leaves with their numerous pellucid dots and dark spots of hypericin are also characteristic. If you squeeze a fresh bud between your thumbnails, it will produce a freely exuding liquid, a bright red, resinous pigment which contains multiple bioactive compounds.

There are two main types of active compounds in *Hypericum perforatum*: the dianthrones and the flavanoids. The activity of the whole herb is best represented by a liquid extract of the fresh or recently dried flowering tops. The herb yields its properties to hot water, alcohol and oil, with alcohol providing the most complete extraction.

The red pigments are located in the buds and the flowers, as well as in the idioblasts of the leaves. These pigments denote the presence of dianthrones (hypericins), a rather unstable but extremely active class of constituents. In chromatographic analysis of this herb, the fluorescent red pigments gravitate to one spot, resting above layer after layer of verticolored flavanoids.

The flavanoids (hyperoside, rutin, quercitin, isoquercitrin, luteolin, etc.) are located in the flowers and in the leaves. These flavanoids provide a slightly sedative, diuretic and anti-inflammatory effect. They work closely with the hypericins, and are a highly significant part of this whole herb.

The tannin content of the herb is about 10%, accounting for its historical use as an astringent and antidiarrheal. The macerated oil of fresh *Hypericum perforatum* flowers contains hyperforin, which provides a wound-healing and antibiotic influence (Brondz et al, *Tetrahedron Lett* 23, 1982). This is a compound which increases in concentration in the plant during the development of fruit and seeds, therefore oil extractions are best performed using herb harvested as the plant begins to mature its fruit and seed.

Most extracts of *Hypericum perforatum* that are sold commercially provide a 300 mg dose that contains 0.3% hypericin, but this can vary. Many of the available prescriptions of St. John's Wort are standardized for their hypericin content, and not necessarily for the other compounds such as flavanoids. The reason most of the extracts purchased over-the-counter have 0.3% hypericin in a 300 mg dose is because they are based on a European formulation that has been used as a standard in the various studies conducted over the years. This formulation is called Jarsin, or LI 160.

*Hypericum* extracts have been shown to cause a 50% inhibition of serotonin uptake by rat brain cells. Whenever a brain impulse occurs, serotonin is released from one brain cell, influences a receptor on an adjoining cell, and then much of it is returned to the original cell to be used again or degraded. Prozac, and other similar antidepressants, such as Zoloft and Paxil, work by inhibiting the re-uptake of serotonin. This is why they are referred to as serotonin re-uptake inhibitors. As a consequence of this re-uptake inhibition, more serotonin stays around to influence brain cells, and mood is elevated.

Another way that pharmaceutical antidepressants work is by inhibiting an enzyme called monoamine oxidase (MAO). This enzyme degrades many brain chemicals including serotonin, norepinephrine, epinephrine and especially dopamine. By inhibiting this enzyme, most of the brain chemicals stay in our brain, leading to enhanced alertness and mood elevation. It seems that some compounds within *Hypericum perforatum* (probably hypericins and flavanols) also have the ability to inhibit this enzyme (Bladt and Wahner, *J. Geriatr. Psychiatry Neurol.* 7:S57–59, 1994; Thiede and Walper, *J. Geriatr. Psychiatry Neurol.* 7:S54–56, 1994).

After you swallow a pill of *Hypericum perforatum*, it will start becoming apparent in your bloodstream roughly within an hour or two (Kerb, *Antimicrob. Agents Chemother.* 40:2087–2093, 1996). The higher the dose, the quicker it is found in the bloodstream. It is estimated that about 20% of the hypericin is absorbed. A dose of 0.75 mg of hypericin lasts in the bloodstream for more than a day.

Today, *Hypericum perforatum* is used primarily for treating mild to moderate depression and related disorders (Linde et al, *British Med. J.* 313:253–258, 1996). Germany's Kommission E (the agency that regulates herbs and other natural remedies, equivalent to the FDA's regulation of pharmaceuticals in the U.S.A.) lists the indications for the use of *Hypericum perforatum* in the treatment of psychovegitative disturbances, depressive states, fear and nervous disturbances. In addition, to *Hypericum perforatum*'s use as a natural remedy in the treatment of depression, the herb has demonstrated antiviral and antibacterial capabilities. Studies indicate that hypericin, the active component of *Hypericum perforatum*, inhibits the capability of the offspring of certain viruses to replicate (Lavie et al, *Transfusion* 35:392–400, 1995). Additionally, it was found that hypericin also appeared to directly inactivate the replication process of certain viruses that previously had the capability. Viruses studies include HIV (Hudson et al, *Science* 254:522, 1991), herpes simplex virus type I and II, Epstein-Barr virus and influenza types A and B. *Hypericum perforatum* also appears to have broad spectrum anti-microbial activity. The organisms studies include *Staphylococcus aureus* (Staph), *Streptococcus mutans* (Strep) and *Escherichia coli* (*E. coli*).

A 1994 double-blind, placebo-controlled study showed that *Hypericum* extracts gave the benefit of increased deep sleep during the total sleeping period of the patients (Schulz, *J. Geriatry Psych. Neurol.* 7:S39–43, 1994).

Hypericin, one of the active agents from *Hypericum perforatum*, has been also shown in various studies to work effectively against cancerous cells and tumors of varying kinds. In 1996, Werf et al (*Lanryngyscope* 106:479–483) reported that hypericin shows great potential in targeting human cancer growths through what is called "phototargeting", a process that uses laser activation of hypericin, along with chemotherapy, for improved results in inhibiting the growth of cancerous cells.

Oils derived from *Hypericum perforatum* has long been held in high esteem for treatment of all types of abrasions and wounds. The oil, which does not contain hypericin, but another valuable compound known as hyperforin, which is mainly responsible for the oil's therapeutic properties. Though somewhat difficult to isolate and preserve for extended periods of time, hyperforin has shown considerable promise as a primary component in salves or dressings for topical and other wounds. It only makes sense that in being able to withstand and inhibit bacterial and viral growth, *Hypericum perforatum* can effectively aid topical wounds in their healing and recovery.

Although some health care providers have suggested that *Hypericum perforatum* may be used to treat a variety of ailments, such as those described above, nowhere has there been any use, or suggestion of use, of this compound for the treatment of amyloid formation, deposition, accumulation and/or persistence, such as that which occurs in the amyloidoses, including Alzheimer's disease. The present invention clearly demonstrates the effectiveness of *Hypericum perforatum* and derivatives thereof obtained from different commercial sources for the 1) inhibition of Alzheimer's Aβ amyloid fibril formation (important for patients in early to mid-stage Alzheimer's disease), 2) inhibition of Alzheimer's amyloid fibril growth (important for patients in early to mid-stage Alzheimer's disease), 3) inhibition of Alzheimer's amyloid-PG/GAG interactions (important for patients in all stages of Alzheimer's disease) and 4) causing the dissolution/disruption of preformed Alzheimer's disease amyloid fibrils. In addition, the present invention demonstrates that *Hypericum perforatum* is effective in causing the dissolution of islet amyloid fibrils (ie. amylin) and therefore may serve as an effective treatment for ~90% of type II diabetic patients who have islet amyloid accumulation in the pancreas.

The Examples illustrated below all serve well to establish that, at least in vitro, *Hypericum perforatum* has the ability to inhibit the formation of brain amyloid deposits that occur during normal aging and in a variety of brain disorders including Alzheimer's disease. In addition, it is known that patients who accumulate brain amyloid deposits eventually lose cognitive ability and memory function and sustain a marked reduction in mental clarity in general. Therefore it follows that inhibition of such brain amyloid deposits will at least promote mental alertness in such patients.

The Examples also establish that again, at least in vitro, *Hypericum perforatum* has the ability to reduce, eliminate, prevent, inhibit or disrupt/dissolve amyloid fibril or protein deposits, brain associated amyloid fibril deposits or brain associated amyloid protein deposits, as well as amyloid fibril formation and growth or age associated amyloid fibril formation and growth, brain associated amyloid fibril formation and growth, and interaction of amyloid protein with glycosaminoglycans, or with proteoglycans. In addition, it is known that patients who accumulate amyloid fibril or protein deposits, brain associated amyloid fibril deposits or brain associated amyloid protein deposits, or who display symptoms of amyloid fibril formation and growth or age associated amyloid fibril formation and growth, brain associated amyloid fibril formation and growth, or interaction of amyloid protein with glycosaminoglycans, or with proteoglycans in general will eventually lose mental acuity, mental alertness, concentration, cognitive well being, or some measure of brain function, or cognitive ability, mental performance or memory, or concentration and mental sharpness, or mental vitality, or mental clarity and alertness, short term memory, or some of the ability to learn or remember. It is also known that such patients are subject to age associated or related cognitive or memory decline, or will sustain a marked reduction in mental clarity. It follows that inhibition, reduction, elimination, prevention, disruption, or dissolution of such amyloid fibril or protein deposits, brain associated amyloid fibril deposits or brain associated amyloid protein deposits, or amyloid fibril formation and growth or age associated amyloid fibril formation and growth, brain associated amyloid fibril formation and growth, or interaction of amyloid protein with glycosaminoglycans or with proteoglycans, will improve mental acuity, promote mental alertness, provide nutritional support for age related cognitive or memory decline, promote cognitive well being, support brain function, improve cognitive ability, mental performance or memory, promote concentration and mental sharpness, improve mental vitality, promote greater mental clarity and alertness, improve short term memory, reduce or reverse age associated cognitive or memory decline, support normal brain function, enhance learning or memory; improve concentration, enhance mental performance, reduce mental decline, reduce likelihood of age related brain disorders, and maintain good brain health, in such patients.

The Examples further establish that, at least in vitro, *Hypericum perforatum* has the ability to reduce, eliminate, prevent, inhibit or disrupt/dissolve amyloid fibril or protein deposits, pancreas associated amyloid fibril or protein deposits, as well as amyloid fibril formation and growth, pancreas associated amyloid fibril formation and growth, and pancreas interactions of amyloid protein with glycosaminoglycans or with proteoglycans. In addition, it is known that patients who accumulate amyloid fibril or protein deposits, pancreas associated amyloid fibril or protein deposits, or who display symptoms of amyloid fibril formation and growth, pancreas associated amyloid fibril formation and growth, or pancreas associated interaction of amyloid protein with glycosaminoglycans or with proteoglycans, in general lose healthy pancreatic function, or sustain a reduction in normal insulin function, leading to loss or reduction of pancreatic function. It therefore follows that inhibition, reduction, elimination, prevention, disruption, or dissolution of such amyloid fibril or protein deposits, pancreas associated amyloid fibril or protein deposits, or amyloid fibril formation and growth, pancreas associated amyloid fibril formation and growth, or pancreas associated interaction of amyloid protein with glycosaminoglycans or with proteoglycans, will support healthy pancreatic function and promote pancreatic function by helping to promote normal insulin function in such patients.

EXAMPLES

The following examples are put forth so as to provide those with ordinary skill in the art with the disclosure and description of the identification and use of commercially available *Hypericum perforatum* to inhibit amyloid fibril formation, inhibit amyloid fibril growth, inhibit amyloid-PG/GAG interactions, and cause dissolution/disruption of preformed amyloid fibrils. However, it should not be construed that the invention is limited to these specific examples.

Example 1

*Hypericum Perforatum* Causes a Dose-Dependent Inhibition of Alzheimer's Aβ(1-40) Amyloid Fibril Formation A previously described method of measuring amyloid fibril formation utilizing Thioflavin T fluorometry (H Naiki et al, *Lab. Invest.* 65:104–110, 1991; H Levine III, *Protein Sci.* 2:404–410, 1993; H Levine III, *Amyloid: Int. J. Exp. Clin. Invest.* 2:1–6, 1995; H Naiki and K. Nakakuki, *Lab. Invest.* 74:374–383, 1996) was employed initially to identify whether *Hypericum perforatum* was capable of inhibiting Alzheimer's Aβ1-40 amyloid fibril formation. Using this sensitive assay, any decreases or increases in fluorescence was previously shown to correlate with a decrease or increase in the amount of amyloid fibrils (H Naiki et al, *Lab. Invest.* 65:104–110, 1991; H Levine III, *Protein Sci.* 2:404–410, 1993: H Levine III, *Amyloid: Int. J. Exp. Clin. Invest.* 2:1–6, 1995; H Naiki and K. Nakakuki, *Lab. Invest.* 74:374–383, 1996), allowing one to determine the identity and extent of potential inhibitors and/or enhancers of amyloid fibril formation.

In one study, the dose-dependent effects of *Hypericum perforatum* on Alzheimer's Aβ(1-40) fibril formation was assessed by Thioflavin T fluorometry. Thioflavin T is known to bind to fibrillar amyloid proteins, and an increase in fluorescence correlates with an increase in amyloid fibril formation, whereas a decrease in fluorescence correlates with a decrease in amyloid fibril formation. The Alzheimer's Aβ protein (1-40) when incubated at 37° C. tends to spontaneously form amyloid fibrils which increase in quantity over time. In this study, we tested for *Hypericum perforatum*'s ability to inhibit the Alzheimer's amyloid Aβ protein from forming fibrils over a 1 week period. For these studies, 300 μl of 25 μM Aβ(1-40)(Bachem Inc., Torrance, Calif., USA; Lot #T20824) in 150 mM TRIS, 10 mM NaCl, pH 7.0 (TBS) was incubated in microcentrifuge tubes at 37° C. for 1 week (in triplicate), either alone, or in the presence of increasing concentrations (i.e. 0.01 µl, 0.1 µl, 0.5 µl and 1.0 µl) of a water extract (described below) obtained from the gelatin-capsule contents of a commercial source of *Hypericum perforatum* (Future Biotics, Lot #97V736). This commercial source of *Hypericum perforatum* contained 0.3% hypericin standardized extract in each capsule.

For the procedure to generate water extracts of *Hypericum perforatum*, 500 mg of either a) standardized *Hypericum perforatum* obtained from the contents of gelatin-capsules of a commercial source of *Hypericum perforatum* (containing 0.3% hypericin standardized extract) or b) freeze-powdered dried whole plant (i.e. leaves, buds and flowers) of *Hypericum perforatum*, were extracted with 3 ml of distilled water (Baxter) and placed in microcentrifuge tubes. The microcentrifuge tube contents were then vortexed by hand for 3–4 minutes, and then allowing to stand for 1–2 minutes. The samples were then centrifuged on a microcentrifuge (Eppendorf, model 5415C) for 30 minutes at 14,000 ×g (at room temperature). Following centrifugation, the supernatants were collected and designated as the "water extracts". To determine dose-dependent effects of *Hypericum perforatum*, 0.01 µl 0.1 µl, 0.5 µl and 1.0 µl of the water extract was used for testing as described above.

To assess the dose-dependent effects of each *Hypericum perforatum* on Aβ(1-40) fibril formation, 50 µl aliquots were taken from each tube (as described above) for analysis at 1 hr, 1 day, 3 days, and 1 week. For each determination described above, following each incubation period, 50 µl of Aβ+/−increasing concentrations of a water extract of *Hypericum perforatum* were added to 1.2 ml of 100 µM Thioflavin T (Sigma Chemical Co., St. Louis, Mo.) in 50 mM $NaPO_4$ (pH 6.0). Studies indicated that increasing concentrations of fibrillized Aβ gave a proportional increase in fluorescence in the presence of 100 µM Thioflavin T, ruling out the presence of any disproportionate inner filter effects in these studies. Fluorescence emission at 482 nm was measured on a Turner instrument-model 450 fluorometer at an excitation wavelength of 450 nm. For each determination, the fluorometer was calibrated by zeroing in the presence of the Thioflavin T reagent alone, and by seting the 50 ng/ml riboflavin (Sigma Chemical Co., St. Louis, Mo.) in the Thioflavin T reagent to 1800 fluorescence units. All fluorescence determinations were based on these references and any fluorescence given off by any of the compounds tested in the presence of the Thioflavin T reagent was always subtracted from all pertinent readings.

For all fibrillogenesis studies utilizing Thioflavin T fluorometry, as disclosed herein, comparisons of amyloid protein in the presence or absence of test compounds were based on paired Student's t tests with data shown as mean +/− standard deviation. Significance was reported at the 95% ($p<0.05$), 99% ($p<0.01$) and 99.999% ($p<0.001$) confidence levels.

As shown in FIG. 1, the effects of various amounts (i.e. 0.01 µl, 0.1 µl, 0.5 µl and 1.0 µl) of *Hypericum perforatum* on Alzheimer's Aβ(1-40) amyloid fibril formation was evaluated over a 1-week incubation period. Freshly suspended Aβ(1-40) alone, following a 1-hour incubation at 37° C., demonstrated an initial fluorescence of 126 +/−10 fluorescence units. During the 1-week incubation period, there was a gradual increase in the fluorescence of Aβ(1-40) alone, increasing 5.4-fold from 1 hour to 3 days, with a peak fluorescence of 682 +/−157 fluorescence units observed at 3 days (FIG. 1). A significant inhibition ($p<0.001$) of Aβ1-40 amyloid fibril formation by 0.5 µl and 1.0 µl of *Hypericum perforatum* was detected as early as 1 hour of incubation. Significant dose-dependent inhibition by increasing concentrations of *Hypericum perforatum* on Aβ1-40 amyloid fibril formation was observed at all time points including 1 hour, 1 day, 3 days and 1 week. At 1 day, 0.5 µl and 1.0 µl of a water extract of *Hypericum perforatum* inhibited Aβ1-40 amyloid fibril formation by 88% and 93%, respectively. At 3 days, 0.5 µl and 1.0 µl of a water extract of *Hypericum perforatum* inhibited Aβ1-40 amyloid fibril formation by 81% and 94%, respectively. At 1 week, increasing concentrations of *Hypericum perforatum* inhibited Aβ1-40 fibril formation in a dose-dependent manner, such that 0.1 µl, 0.5 µl and 1.0 µl of a water extract of *Hypericum perforatum* inhibited Aβ1-40 amyloid fibril formation by 54%, 87% and 96%, respectively. This initial data indicated that *Hypericum perforatum* was a potent inhibitor of Alzheimer's amyloid fibril formation and exerted its effects in a dose-dependent manner.

Example 2

*Hypericum Perforatum* Inhibits Alzheimer's Amyloid Fibril Growth

In Alzheimer's disease and other amyloidoses, amyloid fibril growth is believed to involve amyloid protein self-interactions (ie. Aβ-Aβ interactions). Any potential effective therapeutic agent for amyloid deposition, accumulation and/or persistence should also be capable of causing an inhibition of amyloid protein self-interactions. This is important for preventing any new amyloid fibril formation when treating Alzheimer's disease patients at early stages of the disease. ELISA methodologies (i.e. solid phase binding assays) were therefore used to identify compounds which were capable of inhibiting Aβ-Aβ interactions (i.e. Alzheimer's amyloid fibril growth).

Aβ(1-40) was first labelled with biotin according to the following protocol. 1 mg of Aβ(1-40) (Bachem Inc., Torrance, Calif., USA; Lot #WL934) was dissolved in 200 µl of PBS (pH 8.0) and incubated for 1 week at 37° C. The fibrillar Aβ solution was then added to 0.2 mg of a biotinylation agent [(sulfosuccinimidyl-6-(biotinamido) hexanoate)] (sulfo-NHS-LC-Biotin) and incubated for 45 minutes at room temperature (according to the manufacturer's protocol; Pierce). To remove excess sulfo-NHS-LC-Biotin not incorporated into Aβ, 25 µl of 3M sodium acetate and 1 ml of ethanol were added to the solution, vortexed and then centrifuged at 14,000×g for 20 minutes. The supernatant was then discarded and the pellet was resuspended in 200 µl of distilled water, and reprecipitated with ethanol containing 2.5% of 3M sodium acetate. The centrifugation steps (described above) were then repeated. The pellet which contained fibrillized Aβ which was biotinylated (at the non selfinteracting region of Aβ) was then resuspended in 1 ml of distilled deionized water. The amount of biotin incorporated was then determined using the HABA (2-(4'-hydroxyazo-benzene)benzoic acid) method (according to the manufacturer's protocol; Pierce).

2 µg of unlabelled Aβ in 40 µl of Tris-buffered saline containing 100 mM Tris-HCl, 50 mM NaCl, 3 mM $NaN_3$, pH 7.0 (TBS) was allowed to bind overnight at 4° C. to microtiter wells (Nunc plates, Maxisorb).The next day all of the microtiter wells were blocked for 2 hours by incubating with 300µl of TBS with 0.05% Tween-20 (TTBS) plus 2% bovine serum albumin (BSA)(obtained from the Sigma Chemical Company, St. Louis, Mo., USA). Then, 100 µl of 12.5 µM biotinylated Aβ1-40 in TTBS, in the presence or absence of 1 µl of water extracts (described above) were placed in wells (in triplicate) containing substrate bound unlabelled Aβ or blank, and allowed to bind overnight at 4° C. The next day, the wells were rinsed 3 times with TTBS, and then probed for 2 hours with 100 µl of streptavidin-peroxidase or anti-biotinperoxidase (1:500 dilution of a 2 µg/ml solution)(Sigma Chemical Co., St. Louis, Mo.) in TTBS containing 0.1% BSA. The wells were then rinsed 3 times with TTBS and 100 µl of a substrate solution (OPD-Sigma Fast from Sigma Chemical Co., St. Louis, Mo.) was added to each well and allowed to develop for 5 minutes or until a significant color change was observed. The reaction was stopped with 50 µl of 4N $H_2SO_4$ and read on a Model 450 microplate reader (Biorad, Hercules, Calif., USA) at 490 nm.

The compounds tested included *Hypericum perforatum* obtained from a water extract (extracted as described in example 1) of freeze-powdered dried plant materials (whole plant including leaves, buds and flowers; obtained from The Herbalist, Seattle, Wash., U.S.A.) or from the powdered contents of gelatin-coated capsules containing standardized *Hypericum perforatum* extract (i.e. 0.3% hypericin) obtained commercially (Sundown Herbals, Lot #04228 04-01).

Figure 2:
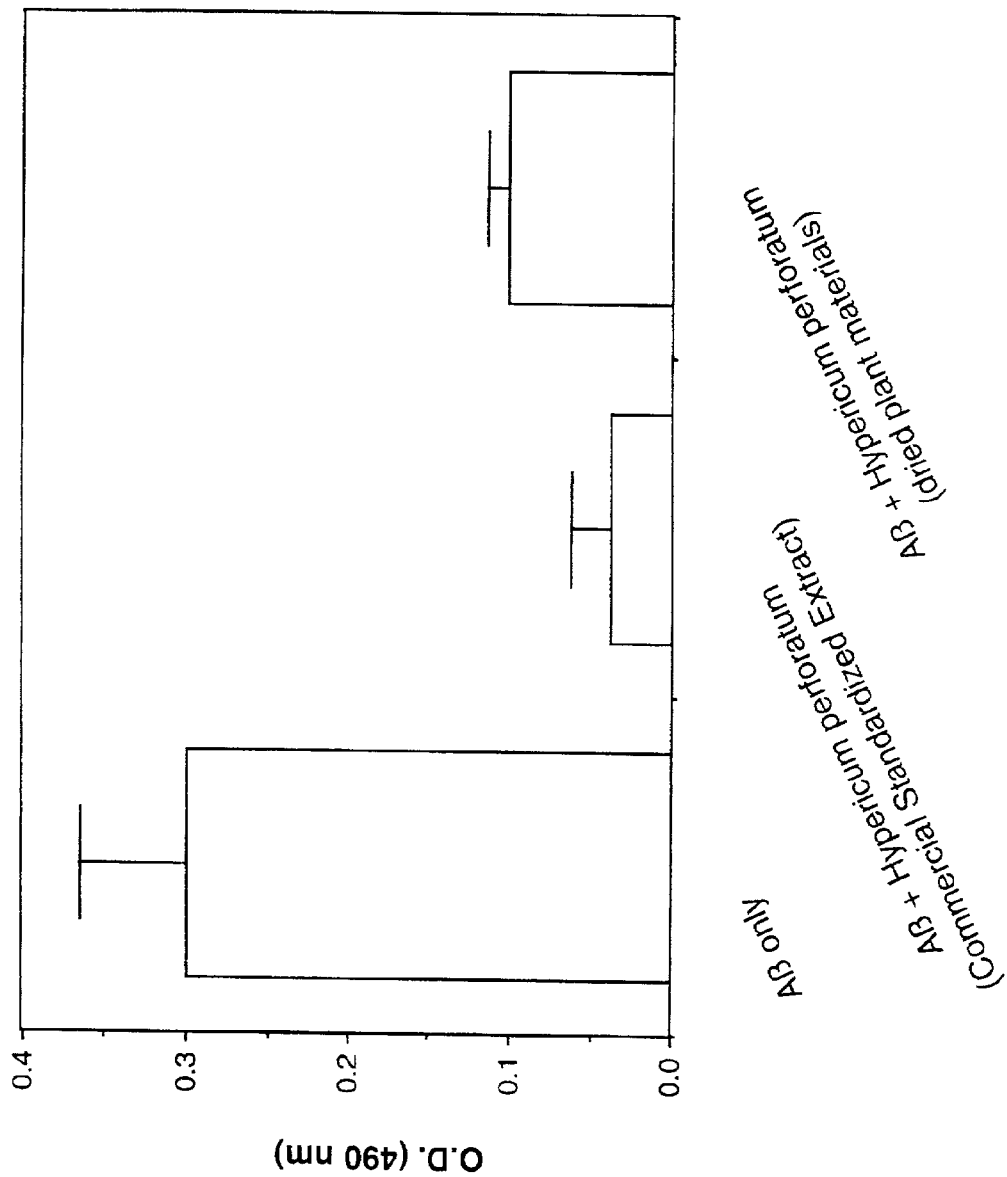
FIG. 2 is a black and white graph of a solid phase binding assay utilized to identify lead compounds which inhibit Alzheimer's Aβ-Aβ interactions (i.e. Alzheimer's amyloid fibril growth). *Hypericum perforatum* (derived either from an extract obtained from dried plant materials, or from an extract obtained from the powder present in commercially available gelatin-capsules which contain 0.3% hypericin) are potent inhibitors of Alzheimer's amyloid fibril growth.

As shown in FIG. 2, *Hypericum perforatum* extract obtained from freeze-powdered dried plant materials, and from a commercial source (containing 0.3% standardized extract) were effective in causing a significant reduction in Aβ-Aβ interactions. Commercially available standardized *Hypericum perforatum* extract (containing 0.3% hypericin) caused a significant ($p<0.001$) 88% inhibition of Aβ-Aβ interactions, whereas *Hypericum perforatum* extract obtained from freeze-powdered dried plant materials caused a significant ($p<0.001$) 66% inhibition of Aβ-Aβ interactions. These data demonstrated that *Hypericum perforatum* was a potent inhibitor of Aβ-Aβ interactions, indicative of amyloid fibril growth.

Example 3

*Hypericum Perforatum* Inhibits Aβ-Glycosaminoglycan Interactions

One study was implemented to determine whether *Hypericum perforatum* was an effective inhibitor of Aβ-proteoglycan/glycosaminoglycan (PG/GAG) interactions. Since PGs/GAGs have been found to accumulate in amyloid deposits and are believed to prevent the body's natural ability to remove unwanted "amyloid" (reviewed in Snow and Wight, *Neurobiology Aging* 10:481–497, 1989), an inhibitor of Aβ-PG/GAG interactions is a desirable additional target for an amyloid therapeutic. In this study a solid phase binding immunoassay was utilized to determine whether *Hypericum perforatum* obtained from dried plant materials or from the powdered contents of gelatin-coated capsules containing standardized *Hypericum perforatum* extract (i.e. 0.3% hypericin) obtained commercially was an effective inhibitor of Aβ-PG/GAG interactions.

12 µg of perlecan glycosaminoglycans (isolated from the Engelbreth-Holm-Swarm sarcoma as previously described (Castillo et al, *J. Neurochemistry* 69:2452–2465, 1997) in 40 µl of Tris-buffered saline containing 100 mM Tris-HCl, 50 mM NaCl, 3 mM $NaN_3$, pH 7.0 (TBS) was allowed to bind overnight at 4° C. to microtiter wells (Nunc plates, Maxisorb). The next day all of the microtiter wells were blocked for 2 hours by incubating with 300 µl of TBS with 0.05% Tween-20 (TTBS) plus 1% bovine serum albumin (BSA). 100 µl of Aβ1-40 (12.5 µM) (Bachem Inc., Torrance, Calif., USA; Lot ##T20824)) in TTBS containing 1% albumin in the presence or absence of 1 µl of a water extract of *Hypericum perforatum* were placed in wells (in triplicate) containing substrate bound perlecan GAGs or blank, and allowed to bind overnight at 4° C. The next day, the wells were rinsed 3 times with TTBS, and then probed for 2 hours with 100 µl of biotinylated anti-4G8 and anti-6E10 (Senetek. Maryland Heights, Mo.) diluted 1:2000 with TTBS. Bound antibodies were then probed with 100 µl of streptavidin-peroxidase or anti-biotinperoxidase (1:500 dilution of a 2 µg/ml solution; Sigma Chemical Co., St. Louis, Mo.) in TTBS for 1 hour. The wells were then rinsed 3 times with TTBS and 100 µl of a substrate solution (OPD-Sigma Fast from Sigma Chemical Co., St. Louis, Mo.) was added to each well and allowed to develop for 5 minutes or until a significant color change was observed. The reaction was stopped with 50 µl of 4N $H_2SO_4$ and read on a Model 450 microplate reader (Biorad, Hercules, Calif., USA) at 490 nm.

For the study, the compounds tested included *Hypericum perforatum* obtained from a water extract (extracted as described in example 1) of dried plant materials (whole plant including leaves, buds and flowers; obtained from The Herbalist, Seattle, Wash., U.S.A.) or from the powdered contents of gelatin-coated capsules containing standardized *Hypericum perforatum* extract (i.e. 0.3% hypericin) obtained commercially (Sundown Herbals, Lot #04228 04-01).

Figure 3:
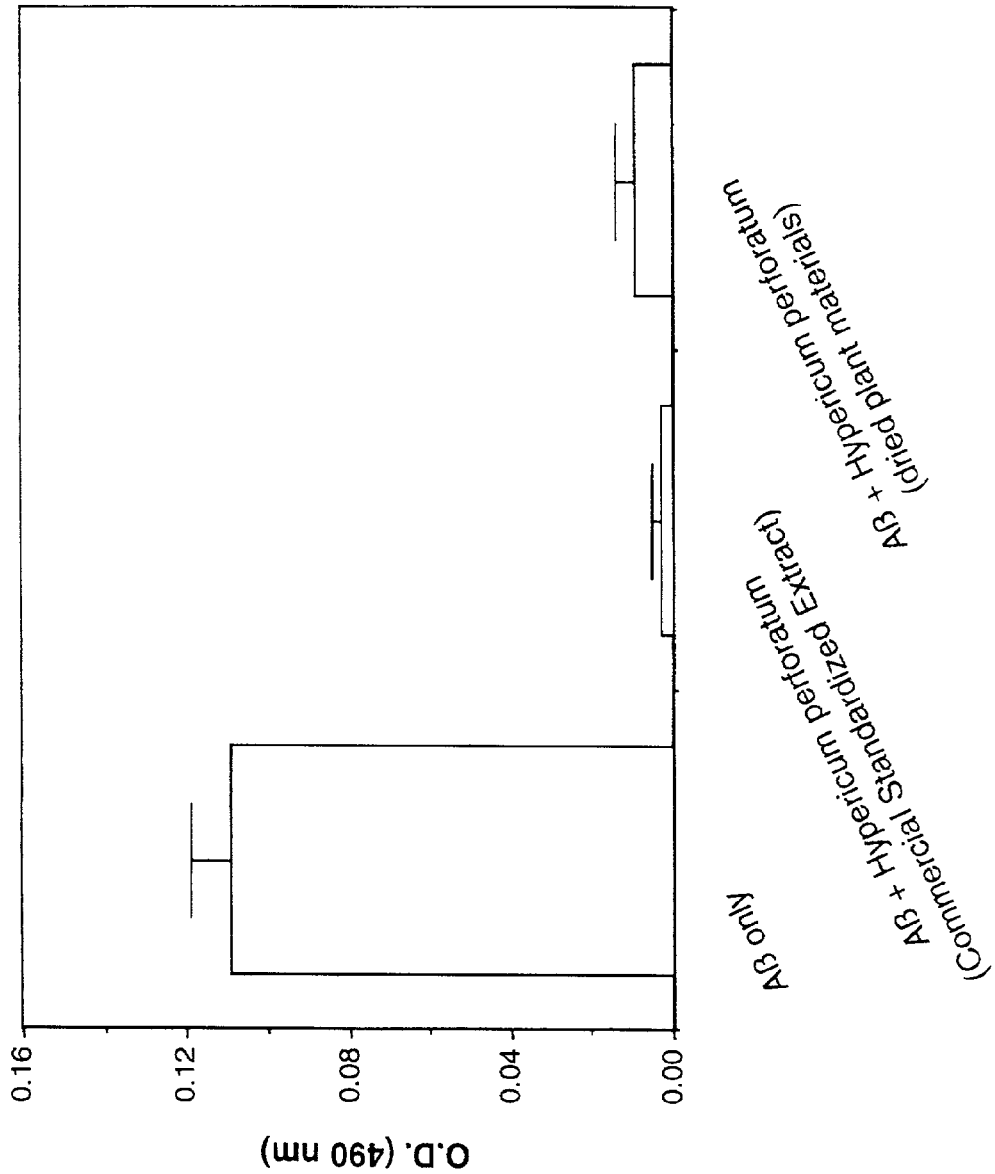
FIG. 3 is a black and white graph of a solid phase binding immunoassay utilized to determine the potential dose-dependent effects of *Hypericum perforatum* (derived either from an extract obtained from dried plant materials, or from an extract obtained from the powder present in commercially available gelatin-capsules which contain 0.3% hypericin) on inhibition of Aβ-Perlecan GAG interactions. Significant dose-dependent inhibition of Aβ-perlecan GAG interactions is observed with treatment of *Hypericum perforatum*.

As shown in FIG. 3, *Hypericum perforatum* obtained from whole plant materials significantly ($p<0.001$) inhibited Aβ-perlecan GAG interactions by 92%. In addition, *Hypericum perforatum* obtained from a standardized extract (containing 0.3% hypericin) was also a most potent inhibitor (by 97%; $p<0.001$) of Aβ-perlecan GAG interactions. These data demonstrated that *Hypericum perforatum* was also capable of inhibiting Aβ-PG/GAG interactions.

Example 4

*Hypericum Perforatum* Causes a Dissolution/Disruption of Pre-Formed Alzheimer's Disease Amyloid 1-40 Fibrils in a Dose-Dependent Manner and Within a 2-Hour Period One study was implemented to determine whether *Hypericum perforatum* extracts were capable of causing a "dissolution" or "disruption" of pre-formed Alzheimer's disease amyloid fibrils. This type of activity would be important for any potential anti-amyloid drug which can be used in patients who already have substantial amyloid deposition in organs and/or tissues. For example, Alzheimer's disease patients in mid-to late stage disease have abundant amyloid deposits in their brains as part of both neuritic plaques and cerebrovascular amyloid deposits. A natural therapeutic agent capable of causing dissolution of pre-existing amyloid would be advantageous for use in these patients who are at latter stages of the disease process.

For this study, 1 mg of Aβ(1-40)(Bachem Inc., Torrance, Calif., USA; Lot #T20824) was dissolved in 1.0 ml of double distilled water (1 mg/ml solution) and then incubated at 37° C. for 1 week to cause abundant Alzheimer's amyloid fibril formation. 25 µM of fibrillized Aβ was then incubated in triplicate for 2 hours at 37° C. in a total final volume of 60 µl TBS, in the absence or presence of increasing concentrations (i.e. 0.01 µl, 0.1 µl, 0.5 µl, and 1.0 µl) of *Hypericum perforatum* water extracts derived from either freeze-powdered whole dried plant materials (whole plant including leaves, buds and flowers; obtained from The Herbalist, Seattle, Wash., U.S.A.) or from the powdered contents of gelatin-coated capsules containing standardized *Hypericum perforatum* extract (i.e. 0.3% hypericin) obtained commercially (Sundown Herbals, Lot #04228 04-01). Following a 2 hour incubation, 50 µl aliquots were added to 1.2 ml of 100 µM Thioflavin T (Sigma Chemical Co., St. Louis, Mo.) in 50 mM NaPO$_4$ (pH 6.0) for fluorometry readings as described in Example 1 above.

For this study, the compounds tested included increasing concentrations of a water extract of *Hypericum perforatum* obtained from freeze-powdered whole dried plant materials or from the powdered contents of gelatin-coated capsules obtained commercially, as described in example 1.

Figure 4:
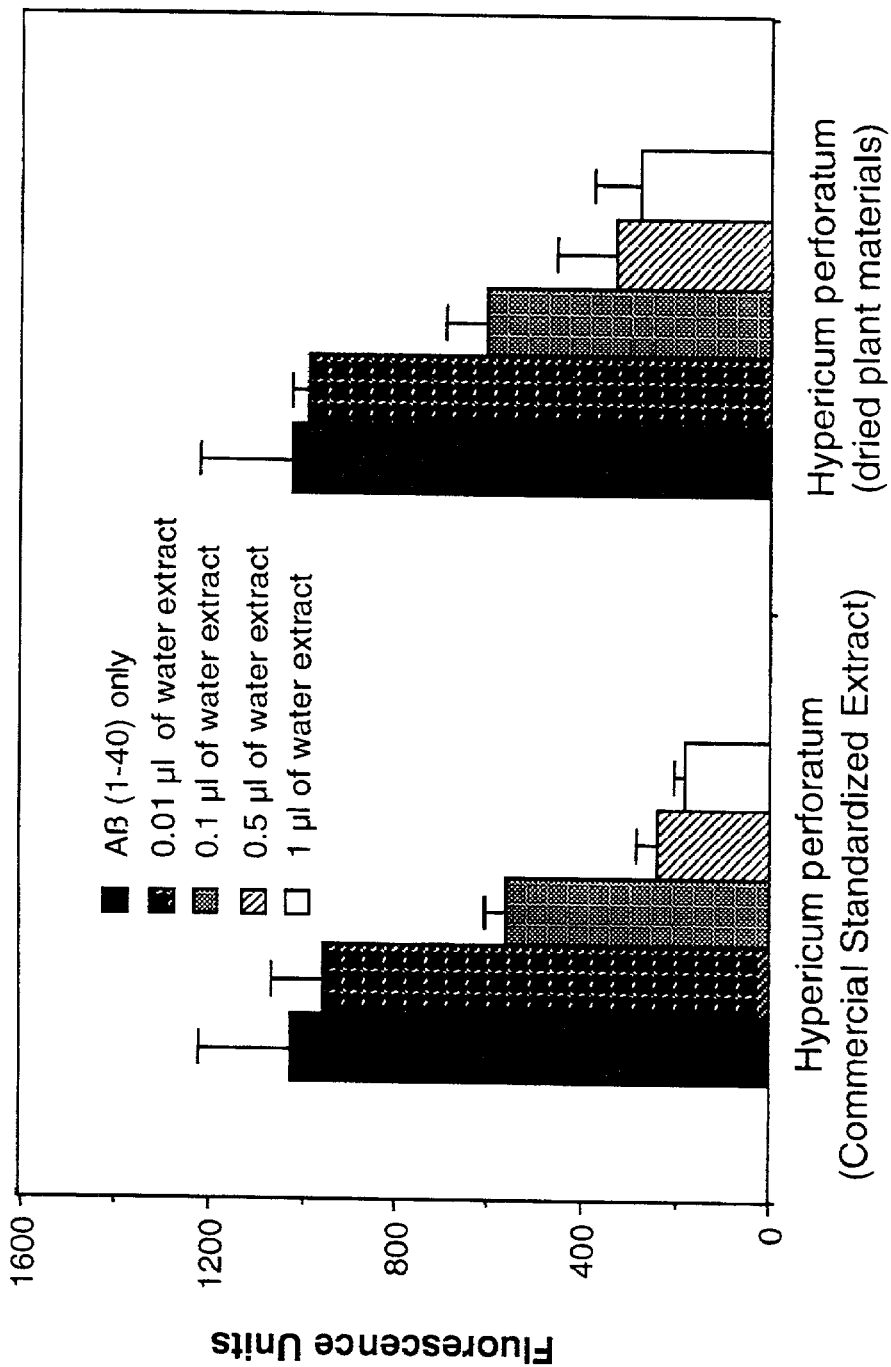
FIG. 4 is a black and white graph of a Thioflavin T fluorometry assay utilized to determine the potential dose-dependent effects of *Hypericum perforatum* on dissolution/disruption of pre-formed Alzheimer's Aβ1-40 amyloid fibrils within a 2 hour incubation period. *Hypericum perforatum* (derived either from an extract obtained from dried plant materials, or from an extract obtained from the powder present in commercially available gelatin-capsules which contain 0.3% hypericin) causes dissolution of pre-formed Alzheimer's Aβ1-40 amyloid fibrils in a dose-dependent manner.

As shown in FIG. 4, both extracts derived from whole dried plant materials and from a commercial source (containing 0.3% hypericin) caused a dose-dependent dissolution/disruption of pre-formed Aβ1-40 fibrils within a 2-hour incubation period. For example, 0.5 µl and 1.0 µl of water extracts derived from a commercial standardized extract of *Hypericum perforatum* caused a significant ($p<0.001$) 77% and 83% dissolution/disruption of Aβ1-40 amyloid fibrils, respectively. Similarly, 0.5 µl and 1.0 µl of a water extract obtained from freeze-powdered whole dried plant materials caused a significant ($p<0.001$) 68% and 73% dissolution/disruption of Aβ1-40 amyloid fibrils, respectively. On the other hand, 0.01 µl of either water extracts from *Hypericum perforatum* did not cause a significant dissolution/disruption of pre-formed Aβ1-40 amyloid fibrils. These data demonstrated that *Hypericum perforatum* causes dissolution of pre-formed Alzheimer's disease amyloid fibrils in a dose-dependent manner. Confirmation of the "dissolution effect" of *Hypericum perforatum* on Alzheimer's disease Aβ1-40 fibrils was demonstrated by Congo red staining assays, whereby a marked reduction of congophilia (i.e. red/green birefringence when viewed under polarized light, and which represents a dissolution/disruption of the amyloid fibrillar structure) was observed when Aβ amyloid fibrils were treated with *Hypericum perforatum* (from either source) for 2 hours (not shown).

Example 5

*Hypericum Perforatum* Causes a Dissolution/Disruption of Aβ(1-42) Alzheimer's Amyloid Fibrils The amyloid fibrils of Alzheimer's disease primarily consist of Aβ in a form containing residues 1-40 or 1-42. The longer variant of Aβ contains two hydrophobic residues which cause substantial fibril formation almost immediately (Castillo et al, *J. Neurochem.* 69:2452–2465, 1997). Aβ1-42 is also believed to be the predominant form of Aβ existing in Alzheimer's amyloid plaques, whereas Aβ1-40 is believed to be the predominant form of Aβ existing in Alzheimer's cerebrovascular amyloid deposits (Tamaoka et al, *Br. Res.* 679:151–156, 1995; *Biochem. Biophys. Res. Comm.* 205:834–842, 1994). The next study was therefore implemented to determine whether *Hypericum perforatum* also causes dissolution/disruption of pre-formed Aβ(1-42) amyloid fibrils and whether this effect was long-lasting.

For this study, the method of Thioflavin T fluorometry as described in example 1 was used. Briefly, 60 µl of 25 µM of Aβ(1-42)(Bachem Inc, Torrance, Calif., USA; Lot # 516817) in TBS (pH 7.0) either alone, or containing increasing amounts (i.e. 0.01 µl, 0.1 µl, 0,5 µl, and 1.0 µl) of *Hypericum perforatum* water extracts were incubated in microcentrifuge tubes at 37° C. for 48 hours (in triplicate).

For this study, the compounds tested included increasing concentrations of a water extract of *Hypericum perforatum* obtained from freeze-powdered whole dried plant materials (leaves, buds and flowers obtained from The Herbalist, Seattle, Wash., U.S.A.) or from the powdered contents of gelatin-coated capsules containing standardized extract (i.e. 0.3% hypericin) and obtained commercially (Sundown Herbals, Lot #04228 04-01). Water extracts were prepared as described in example 1.

As shown in FIG. 5, Alzheimer's Aβ(1-42) alone, following a 2 hour incubation at 37° C., demonstrated an initial fluorescence of 1370 +/−97 fluorescence units. Both water extracts of *Hypericum perforatum* derived from either whole dried plant materials or from a commercial source (containing 0.3% hypericin) caused a dose-dependent dissolution/disruption of pre-formed Aβ1-42 fibrils within a 2 hour incubation period. For example, 0.5 µl and 1.0 µl of the commercial standardized extract of *Hypericum perforatum* caused a significant ($p<0.01$) 46% and 72% ($p<0.001$) dissolution/disruption of Aβ1-42 amyloid fibrils, respectively. 0.5 µl and 1.0 µl of a water extract obtained from freeze-powdered whole dried plant materials caused a significant ($p<0.05$) 24% and 55% dissolution/disruption of Aβ1-42 amyloid fibrils, respectively. On the other hand, 0.1 µl and 0.01 µl of either water extracts from *Hypericum perforatum* did not cause a significant dissolution/disruption of pre-formed Aβ1-42 amyloid fibrils. These data demonstrated that *Hypericum perforatum* causes dissolution of pre-formed Alzheimer's disease amyloid fibrils in a dose-dependent manner. Confirmation of the "dissolution effect" of *Hypericum perforatum* on Alzheimer's disease Aβ1-42 fibrils was demonstrated by Congo red staining assays, whereby a marked reduction of congophilia (i.e. red/green birefringence when viewed under polarized light, and which represents a dissolution/disruption of the amyloid fibrillar structure) was observed when Aβ amyloid fibrils were treated with *Hypericum perforatum* (from either source) for 2 hours (not shown).

Example 6

*Hypericum Perforatum* Causes Dissolution/Disruption of Islet Amyloid Fibrils (Amylin)

90% of patients with type II diabetes demonstrate the deposition and accumulation of amyloid fibrils in the islets of Langerhans in the pancreas (Cooper et al, *Proc. Natl. Acad. Sci. USA* 84:8628–8632, 1987). This amyloid protein involved consists of a 37 amino acid protein known as islet amyloid polypeptide or amylin. Islet amyloid is believed to contribute to the destruction of the beta-cells of the pancreas, thus eventually leading many patients to become insulin-dependent (ie. type I diabetes). Amylin has the ability to also form substantial amyloid fibrils immediately when placed in solution. The next study was therefore implemented to determine whether *Hypericum perforatum* also causes dissolution/disruption of another type of amyloidosis, and whether this effect was also long-lasting.

For this study, the method of Thioflavin T fluorometry as described in Example 5 was used. Briefly, 60 µl (final volume) of 25 µM of human amylin (Bachem Inc,Torrance, Calif., USA; Lot # WL934) in TBS (pH 7.0) was incubated in microcentrifuge tubes at 37° C. for 2 days (in triplicate), either alone, or in the presence of increasing amounts (i.e. 0.01 µl, 0.1 µl, 0.5 µl and 1.0 µl) of *Hypericum perforatum*, water extracts.

For this study, the compounds tested included increasing concentrations of a water extract of *Hypericum perforatum* obtained from freeze-powdered whole dried plant materials (leaves, buds and flowers obtained from The Herbalist, Seattle, Wash., U.S.A.) or from the powdered contents of gelatin-coated capsules containing standardized extract (i.e. 0.3% hypericin) and obtained commercially (Sundown Herbals, Lot #04228 04-01). Water extracts were prepared as described in example 1.

As shown in FIG. 6, freshly suspended amylin alone, following a 2-hour incubation at 37° C., demonstrated an initial fluorescence of 1367 +/−12 fluorescence units. Both water extracts of *Hypericum perforatum* derived from either freeze-powdered whole dried plant materials or from a commercial source (containing 0.3% hypericin) caused a dose-dependent dissolution/disruption of islet amyloid (i.e. amylin or islet amyloid polypeptide) fibrils within a 2 hour incubation period. For example, 0.1 µl, 0.5 µl and 1.0 µl of the commercial standardized extract of *Hypericum perforatum* caused a significant (p<0.001) 67%, 91% and 92% dissolution/disruption of amylin amyloid fibrils, respectively. Similarly, 0.1 µl, 0.5 µl and 1.0 µl of a water extract obtained from freeze-powdered whole dried plant materials caused a significant (p<0.001) 54%, 68% and 73% dissolution/disruption of amylin amyloid fibrils, respectively. These data demonstrated that *Hypericum perforatum* causes dissolution/disruption of pre-formed islet amyloid (i.e. amylin) fibrils in a dose-dependent manner. Confirmation of the "dissolution effect" of *Hypericum perforatum* on amylin fibrils was demonstrated by Congo red staining assays, whereby a marked reduction of congophilia (i.e. red/green birefringence when viewed under polarized light, and which represents a dissolution/disruption of the amyloid fibrillar structure) was observed when amylin amyloid fibrils were treated with *Hypericum perforatum* (from either source) for 2 hours (not shown). This study demonstrated that *Hypericum perforatum* is capable of causing significant dissolution/disruption of other forms of amyloid (such as islet amyloidosis).

Further Aspects and Utilizations of the Invention

Therapeutic Applications

One embodiment of the present invention is to formulate prior to administration in a patient, a pharmaceutical formulation comprising *Hypericum perforatum* (and/or its active ingredients) in one or more pharmaceutical acceptable carriers, diluents or excipients. In a preferred embodiment, a patient who has Alzheimer's disease, type II diabetes or any other amyloidosis, would orally consume commercially available *Hypericum perforatum* in pill, tablet, caplet, soft and hard gelatin capsule, lozenge, vegicap, liquid drop, solution, syrup, tea bag, and/or powder form.

In another preferred embodiment *Hypericum perforatum* obtained commercially in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweeting agents or flavoring agents. The compositions of the invention may be formulated so as to provide quick, sustained or delayed response of the active ingredient after administration to the patient. The compositions are preferably formulated in a unit dosage form, each dosage containing from about 1 to about 1000 mg of *Hypericum perforatum* (or its active ingredients), more usually about 400 to about 750 mg of *Hypericum perforatum* (or its active ingredients). However, it will be understood that the therapeutic dosage administered will be determined by the physician in the light of the relevant circumstances including the clinical condition to be treated, the organ or tissues affected or suspected to be affected with amyloid accumulation, and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. For each formulation provided as an example, lowering or raising of the *Hypericum perforatum* (or its active ingredients) concentration will cause a proportional lowering or raising of the other ingredients as indicated. Hard gelatin capsules may be prepared by using 500 mg of *Hypericum perforatum* (or its active ingredients), 400 mg of starch, and 20 mg of magnesium stearate. The above ingredients are mixed and filled into hard gelatin capsules in 920 mg quantities.

A tablet is prepared by using 500 mg of *Hypericum perforatum* (or its active ingredients), 800 mg of microcrystalline cellulose, 20 mg of fumed silicon dioxide and 10 mg of stearic acid. The components are blended and compressed to form tablets each weighing 1230 mg.

An aerosol solution is prepared by using 0.25 active ingredient, 29.75 ethanol, and 70 of propellent 22 (chlorodifluoromethane). The *Hypericum perforatum* (or its active ingredients) is mixed with ethanol. The mixture is added to a portion of the Propellent 22, cooled to −30° C., and transferred to a filling device. The required amount is then fed to a stainless steel container and diluted with the remainder of the propellent. The value units (listed above) are then fitted to the container. Such an aerosol form of *Hypericum perforatum* (or its active ingredients) may be useful for the treatment of amyloids involving the brain (such as Alzheimer's disease, Down's syndrome, prion diseases etc) by using an aerosol or nasal spray. Previous studies have suggested that in these central nervous system amyloidoses the initial form of entry of a possible environmental agent which may be playing a role in pathogenesis may be derived from the outside world through the nasal passages.

Tablets are made by using 120 mg of *Hypericum perforatum* (or its active ingredients), 90 mg of starch, 70 mg of microcrystalline cellulose, 8 mg of polyvinylpyrrolidone (as 10% in water), 9 mg of sodium carboxymethyl starch, 1 mg of magnesium stearate and 1 mg of talc (total=300 mg). *Hypericum perforatum* (or its active ingredients), starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 300 mg.

Capsules each containing 160 mg of medicant are made by using 160 mg of *Hypericum perforatum* (or its active ingredients), 118 mg of starch, 118 mg of microcrystalline cellulose, and 4 mg of magnesium stearate (total=400 mg).

The *Hypericum perforatum* (or its active ingredients), cellulose, starch and magnesium stearate are blended, passed through a No. 45 mesh U.S. sieve, and filled into hard gelatin capsules in 400 mg quantities.

Suppositories each containing 225 mg of *Hypericum perforatum* (or its active ingredients) are made by using 225 mg of *Hypericum perforatum* (or its active ingredients), 2,000 mg of saturated fatty acid glycerides (total=2,225 mg). The *Hypericum perforatum* (or its active ingredients) are passed through a No. 60 mesh U.S. sieve and suspended in the saturated fatty acid glycerides previously melted using the minimum heat necessary. The mixture is then poured into a suppository mold of nominal 2 g capacity and allowed to cool.

Suspensions each containing 50 mg of medicant per 5 ml dose are made by using 50 mg of *Hypericum perforatum* (or its active ingredients), 50 mg of sodium carboxymethyl cellulose, 1.25 ml of syrup, 0.10 ml of benzoic acid solution, flavor, color, and purified water to total 5 ml. The medicant is passed though a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

An intravenous formulation is prepared by using 250 mg of *Hypericum perforatum* (or its active ingredients), and 1000 mg of isotonic saline. The solution of the above ingredients is administered intravenously at a rate of 1 ml per minute to a subject in need of treatment.

In a preferred embodiment the therapeutic compound of the invention can be administered in any pharmaceutically acceptable vehicle. As used herein "pharmaceutically acceptable vehicle" includes, but is not limited to, any and all solvents, sterile liquids, such as water and oils, including those of petroleum, animal, vegetable or synthetic origin, such as peanut oil, soybean oil, mineral oil, sesame oil and the like, dispersion media, coatings, antibacterial and antifungal agents, isotonic and adsorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Supplementary active compounds can also be incorporated into the compositions. Suitable pharmaceutical excipients include starch, glucose, lactose, sucrose, gelatin, malt, rice, fluor, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

In the methods of the invention, amyloid formation, deposition, accumulation and/or persistence in a subject is inhibited by administrating *Hypericum perforatum* (or its active ingredients) in a therapeutic dosage to the subject. The term subject is intended to include living organisms in which amyloidosis can occur. Examples of subjects include humans, monkeys, cows, dogs, sheep, cats, mice, rats, and transgenic species thereof. Administration of the compositions of the present invention to a subject to be treated can be carried out using known procedures, at dosages and for periods of time effective to inhibit amyloidosis in the subject. An effective amount of the therapeutic compound necessary to achieve a therapeutic effect may vary according to factors such as the amount of amyloid already deposited at the organ or tissue site in the subject, the age, sex and weight of the subject, and the ability of the therapeutic compound to inhibit amyloid formation, deposition, accumulation, persistence, and/or to cause dissolution of pre-formed amyloid in the subject. Dosage regimens can therefore be adjusted to provide the optimum therapeutic response. For example, several divided doses may be administered daily or the dose may be proportionally reduced as indicated by the needs of the therapeutic situation. A non-limiting example of an effective dose range for *Hypericum perforatum* (or its active ingredients) is between 400 and 1000 mg/kg of body weight/per day.

Different modes of delivery of *Hypericum perforatum* (or its active ingredients) may be used. Accordingly, a preferred route of administration is oral administration. Alternatively, *Hypericum perforatum* (or its active ingredients) may be administered by other suitable routes such as subcutaneous, intravenous, intraperitoneal, all routes administered by injection. Depending on the route of administration, the active compound may be coated in a material to protect the compound from the action of acids and other natural conditions which may inactivate the compound.

To administer *Hypericum perforatum* (or its active ingredients), it may be necessary to coat the compound with, or co-administer the compound with, a material to prevent its activation. For example, the therapeutic compound may be administered to a subject in an appropriate carrier, for example, liposomes or a diluent. Pharmaceutically acceptable diluents include saline and aqueous buffer solutions. Liposomes include water-in-oil-in-water CGF emulsions as well as conventional liposomes.

The *Hypericum perforatum* (or its active ingredients) may also be administered parenterally or intraperitoneally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions or dispersions and sterile powders for the preparation of sterile injectable solutions or dispersion. In all cases, the composition must be sterile and must be fluid to the extent that easy use in the syringe exists. It must be stable under the conditions of manufacture and storage and must be preserved against the contaminating action of microorganisms such as bacteria and fungi. The vehicle can be a solvent or dispersion medium containing, for example, water, ethanol, polyol (for example glycerol, propylene glycol, and liquid polyethylene glycol, and the like). suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, prabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the therapeutic agent plus any desired ingredients from a previously sterile-filtered solution thereof.

The *Hypericum perforatum* (or its active ingredients) for Alzheimer's disease and other central nervous system amyloidoses may be optimized to cross the blood-brain banier.

Methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In a preferred embodiment, *Hypericum perforatum* (or its active ingredients) may be directly administered to the cerebrospinal fluid by intraventricular injection. In a specific embodiment, it may be desirable to administer *Hypericum perforatum* (or its active ingredients) locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment *Hypericum perforatum* (or its active ingredients) may be delivered in a controlled release system, such as an osmotic pump. In yet another embodiment, a controlled release system can be placed in proximity to the therapeutic target, ie. the brain, thus requiring only a fraction of the systemic dose.

With regards to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

INDUSTRIAL APPLICABILITY

Use of extracts from *Hypericum perforatum*, and use of the ingredients contained within the various commercial preparations of *Hypericum perforatum*, benefit human patients with Alzheimer's disease and other amyloidoses due to *Hypericum perforatum*'s newly discovered ability to inhibit amyloid fibril formation, inhibit amyloid fibril growth, inhibit amyloid-proteoglycan interactions, inhibit amyloid-glycosaminoglycan interactions, and cause dissolution and/or disruption of preformed amyloid fibrils.

In compliance with the statute, the invention has been described in language more or less specific as to structural features. It is to be understood, however, that the invention is not limited to the specific features shown, since the means and construction show comprise preferred forms of putting the invention into effect. The invention is, therefore, claimed in any of its forms or modifications within the legitimate and valid scope of the appended claims, appropriately interpreted in accordance with the doctrine of equivalents.

We claim:

1. A method for inhibiting the formation, growth or persistence of $A\beta$ fibrils or disrupting preformed $A\beta$ fibrils in a patient, the method comprising the step of administering to the patient a therapeutically effective amount of a water extract of plant matter from a plant of the genus *Hypericum*, species *perforatum*.

2. The method of claim 1 wherein the plant matter comprises leaves, flowers or buds of the plant.

3. A method for promoting, maintaining or enhancing in a patient one or more of the mental or cognitive qualities associated with inhibiting the formation, growth or persistence of $A\beta$ fibrils, the qualities selected from the group of mental or cognitive qualities consisting of memory, concentration, and short term memory, the method comprising the step of administering to the patient a therapeutically effective amount of a water extract of plant matter from a plant of the genus *Hypericum*, species *perforatum*.

4. A method for reducing in a patient one or more of the mental or cognitive effects associated with $A\beta$ fibril formation selected from the group of mental or cognitive effects associated with $A\beta$ fibril formation, the effects consisting of age associated cognitive or memory decline and mental decline, the method comprising the step of administering to the patient a therapeutically effective amount of a water extract of plant matter from a plant of the genus *Hypericum*, species *perforatum*.

5. A method for treating in a patient mental states associated with $A\beta$ fibril formation or persistence, the method comprising the step of administering to the patient a therapeutically effective amount of a water extract of plant matter from a plant of the genus *Hypericum*, species *perforatum*.

6. The method of claim 5 wherein the plant matter comprises leaves, flowers or buds of a plant.

* * * * *